US007666600B2

(12) United States Patent
Linnen et al.

(10) Patent No.: US 7,666,600 B2
(45) Date of Patent: Feb. 23, 2010

(54) CROSS-REACTIVE PRIMERS FOR AMPLIFYING THE NUCLEIC ACIDS OF HIV-1 AND HIV-2

(75) Inventors: Jeffrey M. Linnen, Poway, CA (US); Wen Wu, Carlsbad, CA (US)

(73) Assignee: Gen-Probe Incorporated, San Diego, CA (US)

( * ) Notice: Subject to any disclaimer, the term of this patent is extended or adjusted under 35 U.S.C. 154(b) by 175 days.

(21) Appl. No.: 11/837,954

(22) Filed: Aug. 13, 2007

(65) Prior Publication Data

US 2008/0020398 A1    Jan. 24, 2008

Related U.S. Application Data

(62) Division of application No. 11/015,605, filed on Dec. 16, 2004, now Pat. No. 7,255,996.

(60) Provisional application No. 60/531,183, filed on Dec. 19, 2003, provisional application No. 60/584,706, filed on Jun. 30, 2004.

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/23.72; 536/24.3; 536/24.32; 536/24.33

(58) Field of Classification Search .................. None
See application file for complete search history.

(56) References Cited

U.S. PATENT DOCUMENTS

| | | |
|---|---|---|
| 5,283,174 A | 2/1994 | Arnold, Jr. et al. |
| 5,310,651 A | 5/1994 | Alizon et al. |
| 5,399,491 A | 3/1995 | Kacian et al. |
| 5,599,662 A | 2/1997 | Respess |
| 5,688,637 A | 11/1997 | Moncany et al. |
| 5,712,385 A | 1/1998 | McDonough et al. |
| 5,786,177 A | 7/1998 | Moncany et al. |
| 5,827,648 A | 10/1998 | Eastman et al. |
| 5,856,088 A | 1/1999 | McDonough et al. |
| 5,866,319 A | 2/1999 | Alizon et al. |
| 5,962,665 A | 10/1999 | Kroeger et al. |
| 6,001,558 A | 12/1999 | Backus et al. |
| 6,031,091 A | 2/2000 | Arnold, Jr. et al. |
| 6,187,538 B1 | 2/2001 | Eastman et al. |
| 6,232,455 B1 | 5/2001 | Kroeger et al. |
| 6,277,561 B1 | 8/2001 | Guertler et al. |
| 6,303,293 B1 | 10/2001 | Patterson et al. |
| 6,316,183 B1 | 11/2001 | Alizon et al. |
| 6,335,158 B2 | 1/2002 | Brust et al. |
| 6,610,476 B1 | 8/2003 | Chang et al. |
| 6,623,920 B1 | 9/2003 | Bee et al. |
| 2003/0049604 A1 | 3/2003 | Charneau et al. |
| 2003/0091985 A1 | 5/2003 | Alizon et al. |
| 2003/0186219 A1 | 10/2003 | Alizon et al. |
| 2003/0235835 A1 | 12/2003 | Alizon et al. |

FOREIGN PATENT DOCUMENTS

| | | |
|---|---|---|
| EP | 0 736 600 A2 | 10/1996 |
| EP | 0 504 278 B1 | 1/1997 |
| EP | 0 887 427 A | 12/1998 |
| EP | 1 026 263 A | 8/2000 |
| EP | 1 035 220 A | 9/2000 |
| EP | 1 223 227 A2 | 7/2002 |
| EP | 1 344 837 A1 | 9/2003 |
| EP | 1 422 298 A2 | 5/2004 |
| WO | WO 9216180 A2 * | 10/1992 |
| WO | WO 98/58086 A2 | 12/1998 |
| WO | WO 01/04361 A2 | 1/2001 |
| WO | WO 02055741 A2 * | 7/2002 |

OTHER PUBLICATIONS

Abravaya et al., "Performance of a Multiplex Qualitative PCR LCx Assay for Detection of Human Immunodeficiency Virus Type 1 (HIV-1) Group M Subtypes, Group O, and HIV-2", *J. Clin. Microbiology*, 2000, 38(2):716-723, ASM, Washington D.C., USA.
Damond et al., "Quantification of Proviral Load of Human Immunodeficiency Virus Type 2 Subtypes A and B Using Real-Time PCR", *J. Clin. Microbiology*, 2001, 39(12):4264-4268, ASM, Washington D.C. USA.
Giachetti et al., "Highly Sensitive Multiplex Assay for Detection of Human Immunoceficiency Virus Type 1 and Hepatitis C Virus RNA", J. Clin. Microbiol., Jul. 2002, 40(7):2408-2419, ASM, USA.
McDonough et al., "High Throughput Assay for the Simultaneous or Separate Detection of Human Immunodeficiency Virus (HIV) and Hepatitis Type C Virus (HCV)", Infusionsther Transfusionsmed, 1998, 25:164-169, Karger, Basel.
Masciotra et al., "Detection of Simian Immunodeficiency Virus in Diverse Species and or Human Immunodeficiency Virus Type 2 by Using Consensus Primers within the *pol* Region", *J. Clin. Microbiology*, 2002, 40(9):3167-3171, ASM, Washington D.C. USA.
Morandi et al., "Detection of Human Immunodeficiency Virus Type 1 (HIV-1) RNA in Pools of Sera Negative for Antibodies to HIV-1 and HIV-2", *J. Clin. Microbiology*, 1998, 36(6):1534-1538, ASM, Washington, D.C. USA.
Nazábal et al., "Deteccion Directa De La Infeccion Por VIH 1 Y VIH 2 En Individuos Seropositivos Mediante La Amplificacion Del Adn", Biotechnologia Aplicada, 1998, 10(2):129-132, Sociedad Iberolatinoamericana de Biotecnolgio Aplienda a la Salud, La Habana, Cuba (summary in English).
Nedjar et al., "Co-amplification of specific sequences of HCV and HIV-1 genomes by using the polymerase chain reaction assay: a potential tool for the simultaneous detection of HCV and HIV-1", J. Virol. Methods, 1991, 35:297-304, Elsevier Science B.V., Amsterdam, Netherlands.

(Continued)

*Primary Examiner*—Jeffrey S Parkin
*Assistant Examiner*—Louise Humphrey
(74) *Attorney, Agent, or Firm*—Michael J. Gilly

(57) ABSTRACT

Compositions, methods and kits for detecting the nucleic acids of HIV-1, HIV-2, or the combination of HIV-1 and HIV-2. Particularly described are oligonucleotides that are useful as hybridization probes and amplification primers, including cross-reacting hybridization probes and cross-reacting amplification primers, for detecting very low levels of viral nucleic acids.

17 Claims, 1 Drawing Sheet

OTHER PUBLICATIONS

Pieniazek et al., "Identification of mixed HIV-1/HIV-2 infections in Brazil by polymerase chain reaction", AIDS, 1991, 5(11):1293-1299, Current Science, USA.

Pyra et al., "Ultrasensitive retrovirus detection by a reverse transcriptase assay based on product enhancement", *Proc. Natl. Acad. Sci.*, 1994, 91:1544-1548, USA.

Rouet et al., "Field Evaluation of a Rapid Human Immunodeficiency Virus (HIV) Serial Serologic Testing Algorithm for Diagnosis and Differentiation of HIV Type 1 (HIV-1), HIV-2, and Dual HIV-1-HIV-2, Infections in West African Pregnant Women", *J. Clin. Microbiology*, 42(9):4147-4153, ASM, Washington, D.C. USA.

Vet et al. "Multiplex detection of four pathogenic retroviruses using molecular beacons", *Proc. Natl. Acad. Sci.*, 1999, 96:6394-6399, USA.

Weber et al., "Reduction of Diagnostic Window by New Fourth-Generation Human Immunodeficiency Virus Screening Assays", *J. Clin. Microbiology*, 1998, 36(8):2235-2239, ASM, Washington D.C. USA.

\* cited by examiner

CROSS-REACTIVE PRIMERS FOR AMPLIFYING THE NUCLEIC ACIDS OF HIV-1 AND HIV-2

RELATED APPLICATIONS

This application is a divisional of application Ser. No. 11/015,605, filed Dec. 16, 2004, now U.S. Pat. No. 7,255,996, which claims the benefit of U.S. Provisional Application Nos. 60/531,183, filed Dec. 19, 2003, and 60/584,706, filed Jun. 30, 2004. The entire disclosures of these prior applications are hereby incorporated by reference.

GOVERNMENT INTEREST IN INVENTION

Certain aspects of the invention disclosed herein were made with government support under contracts N01-HB-67130 and N01-HB-07148 with the National Heart, Lung and Blood Institute of the National Institutes of Health. The United States government has certain rights in these aspects of the invention.

FIELD OF THE INVENTION

The present invention relates to the subfield of biotechnology concerned with nucleic acid amplification technology. More specifically, the invention relates to individual assays that are capable of detecting the nucleic acids of HIV-1, HIV-2, or the combination of HIV-1 and HIV-2, and further relates to multiplex assays that are capable of detecting the nucleic acids of both HIV-1 and HIV-2 using a probe and/or primers that cross-react with the two analytes.

BACKGROUND OF THE INVENTION

Although the HIV/AIDS pandemic is principally due to infection by HIV-1, a different retrovirus has emerged as another cause of AIDS. This so-called "HIV-2" virus was first isolated from AIDS patients in West Africa in 1986, and was subsequently detected as an infectious agent for the first time in the United States the following year. Fewer than 100 cases of HIV-2 had been reported in the United States through the end of 1994. Despite this seemingly low number, HIV-2 is being identified as the etiologic agent in growing numbers of immunosuppressive diseases that are clinically indistinguishable from AIDS cases that result from HIV-1 infection (Kanki et al., *Science* 232:238 (1986); Kanki et al., *Science* 236:827 (1987); Clavel et al., *Science* 233:343 (1986); Clavel et al., *N. Engl. J. Med.* 316:1180 (1987)). Although HIV-2 is related to HIV-1 by its morphology and tropism for $CD4^+$ cells, it clearly is a distinct virus and not merely an envelope variant of HIV-1.

Indeed, since HIV-2 is only distantly related to HIV-1, with approximately 50% amino acid conservation in the gag and pol proteins and less than 30% conservation in the env gene products, its presence is not effectively detected by serologic assays used for detecting HIV-1 infection (Constantine N T, *AIDS* 7:1 (1993); Markovitz D M, *Ann. Intern. Med.* 118:211 (1993)). As a result, attempts have been made to develop nucleic acid probes that can be used for specifically detecting HIV-2 viral nucleic acids.

Interestingly, the genomes of both HIV-1 and HIV-2 show substantial sequence heterogeneity among different isolates. As a consequence of this heterogeneity, it has been impossible to find substantial regions of absolute sequence conservation between all isolates of HIV-1 or all isolates of HIV-2 (see published European Patent Application EP 0 887 427). Indeed, numerous viral isolates with unique polynucleotide sequences have been identified for each of these viruses, a factor that further complicates the construction of probes for reliable and effective nucleic acid testing.

Since, like HIV-1, HIV-2 also is transmissible through exchange of body fluids, including blood and plasma, it is important to be able to detect infected body fluids before antibodies to the virus are detectable or symptoms are evident in an infected individual. For protection of patients who might otherwise receive an HIV-2-infected body fluid (e.g., whole blood or plasma during transfusion), or products derived from donated blood or plasma, it is particularly important to detect the presence of the virus in the donated body fluid to prevent its use in such procedures or products. It is also important that procedures and reagents used for detecting HIV-2 can detect relatively low numbers of viral copies which may be present in an infected individual, who may be a donor, during the early stages of infection.

Assays and reagents for detecting HIV-2 have been previously disclosed in, for example, U.S. Pat. Nos. 6,020,123, 5,688,637, 5,545,726 and 5,310,651; European Patent Nos. EP 0404625 B1 and EP 0239425 B1; and published European Patent Application Nos. EP 1026236 A2, EP 0887427 A2.

SUMMARY OF THE INVENTION

A first aspect of the invention relates to a method for determining whether a test sample contains an HIV-1 analyte nucleic acid or an HIV-2 analyte nucleic acid. The invented method includes a first step for combining the test sample with a pair of cross-reactive primers. Next, there is a step for amplifying in an in vitro nucleic acid amplification reaction any of a first sequence of the HIV-1 analyte nucleic acid that may be present in the test sample and any of a first sequence of the HIV-2 analyte nucleic acid that may be present in the test sample. This nucleic acid amplification reaction uses a pair of cross-reactive primers that are capable of co-amplifying HIV-1 and HIV-2 nucleic acids. Products of the reaction may include a first HIV-1 amplicon and a first HIV-2 amplicon. Next, there is a step for detecting in a single hybridization reaction any of the first HIV-1 amplicon and any of the first HIV-2 amplicon that may have been synthesized in the amplifying step. A positive result in the hybridization reaction will indicate that the test sample contained at least one of either the HIV-1 analyte nucleic or the HIV-2 analyte nucleic acid. In a preferred embodiment, the in vitro nucleic acid amplification reaction in the amplifying step is either a TMA reaction, a NASBA reaction or a PCR reaction. In another preferred embodiment, the single hybridization reaction in the detecting step involves the use of a cross-reactive probe that can hybridize either to the first HIV-1 amplicon or to the first HIV-2 amplicon. More preferably, the hybridization reaction in the detecting step further includes an HIV-1-specific probe which hybridizes only to the first HIV-1 amplicon and not to the first HIV-2 amplicon. When this is the case, a positive signal indicating hybridization of the cross-reactive probe together with the absence of a positive signal indicating hybridization of the HIV-1-specific probe indicates that the test sample contains the HIV-2 analyte nucleic acid and does not contain the HIV-1 analyte nucleic acid. In an alternative preferred embodiment, there is an additional step for detecting in a hybridization reaction that includes an HIV-1-specific probe, only the first HIV-1 amplicon and not detecting the first HIV-2 amplicon. In this instance, the HIV-1-specific probe hybridizes only to the first HIV-1 amplicon and not to the first HIV-2 amplicon. When this is the case, a positive signal indicating hybridization of the cross-reactive probe together with the absence of a positive signal indicating hybridization of the HIV-1-specific probe indicates that the test sample contains the HIV-2 analyte nucleic acid and does not contain the HIV-1 analyte nucleic acid. In accordance with another preferred embodiment, the cross-reactive probe used in the detecting step is labeled with a homogeneously detectable label. The homogeneously detectable label can be, for example, a chemiluminescent label. In a highly preferred embodiment, when a chemiluminescent label is employed, the detecting step involves detecting with a luminometer, or performing luminometry. In certain other embodiments of the invented method, the in vitro nucleic acid amplification reaction conducted in the amplifying step does not include an analyte-specific pair of primers that amplify the first sequence of the HIV-2 analyte nucleic acid without also being capable of amplifying the first sequence of the HIV-1 analyte nucleic acid. In still other embodiments, a positive result indicating probe hybridization in the detecting step does not distinguish between the presence of the first HIV-1 amplicon and the first HIV-2 amplicon. Stated differently, hybridization of the probe to a complementary target nucleic acid synthesized in the amplification reaction indicates only that HIV-1 or HIV-2 nucleic acids were present in the test sample, without identifying which was present. In yet other embodiments, the in vitro nucleic acid amplification reaction in the amplifying step can further amplify at least a first sequence of at least one analyte nucleic acid which is different from HIV-1 and HIV-2. In this instance the amplification reaction would be a "multiplex" amplification reaction. In a particularly preferred embodiment of the invented method, the nucleic acids of at least one of hepatitis B virus and hepatitis C virus can be amplified in the amplification reaction in addition to HIV-1 and HIV-2 nucleic acids.

A second aspect of the invention relates to a method for particularly determining whether a test sample contains an HIV-1 analyte nucleic acid. The invented method includes a first step for combining the test sample with a pair of cross-reactive primers. Next, there is a step for amplifying in an in vitro nucleic acid amplification reaction any of a first sequence of the HIV-1 analyte nucleic acid that may be present in the test sample, and any of a first sequence of an HIV-2 analyte nucleic acid that may be present in the test sample. This amplification reaction is carried out using a pair of cross-reactive primers that are capable of co-amplifying HIV-1 and HIV-2 nucleic acids. Products of the amplification reaction may include a first HIV-1 amplicon and a first HIV-2 amplicon. Next, there is a step for detecting any of the first HIV-1 amplicon that may have been synthesized in the amplifying step without detecting any of the first HIV-2 amplicon. A positive result in the hybridization reaction will indicate that the test sample contained the HIV-1 analyte nucleic. In a preferred embodiment, the in vitro nucleic acid amplification reaction in the amplifying step is either a TMA reaction, a NASBA reaction or a PCR reaction. When one of these amplification reactions is employed, the detecting step preferably involves hybridizing an HIV-1 specific hybridization probe which is labeled with a homogeneously detectable label. Such labels advantageously do not require physical separation of unhybridized, free probe from specific probe:target duplexes to determine that such duplexes have formed in a hybridization reaction. In certain preferred embodiments, the homogeneously detectable label is a chemiluminescent label. When this is the case, the detecting step may involve detecting with a luminometer, or performing luminometry. In still another embodiment, the in vitro nucleic acid amplification reaction in the amplifying step does not include an analyte-specific pair of primers that amplify the first sequence of the HIV-2 analyte nucleic acid without also being capable of amplifying the first sequence of the HIV-1 analyte nucleic acid. In yet other embodiments, the in vitro nucleic acid amplification reaction in the amplifying step can further amplify at least a first sequence of at least one analyte nucleic acid which is different from HIV-1 and HIV-2. In this instance the amplification reaction would be a "multiplex" amplification reaction. For example, in a particularly preferred embodiment of the invented method the nucleic acids of at least one of hepatitis B virus and hepatitis C virus can be amplified in the amplification reaction in addition to HIV-1 and HIV-2 nucleic acids.

A third aspect of the invention relates to a method for particularly determining whether a test sample contains an HIV-2 analyte nucleic acid. The invented method includes a first step for combining the test sample with a pair of cross-reactive primers. Next, there is a step for amplifying in an in vitro nucleic acid amplification reaction any of a first sequence of the HIV-1 analyte nucleic acid that may be present in the test sample, and any of a first sequence of an HIV-2 analyte nucleic acid that may be present in the test sample. This amplification reaction is carried out using a pair of cross-reactive primers that are capable of co-amplifying HIV-1 and HIV-2 nucleic acids. Products of the amplification reaction may include a first HIV-1 amplicon and a first HIV-2 amplicon. Next, there is a step for detecting any of the first HIV-2 amplicon that may have been synthesized in the amplifying step without detecting any of the first HIV-1 amplicon. A positive result in the hybridization reaction will indicate that the test sample contained the HIV-2 analyte nucleic. In a preferred embodiment, the in vitro nucleic acid amplification reaction in the amplifying step is either a TMA reaction, a NASBA reaction or a PCR reaction. When one of these amplification reactions is employed, the detecting step preferably involves hybridizing an HIV-2 specific hybridization probe which is labeled with a homogeneously detectable label. Such labels advantageously do not require physical separation of unhybridized, free probe from specific probe:target duplexes to determine that such duplexes have formed in a hybridization reaction. In certain preferred embodiments, the homogeneously detectable label is a chemiluminescent label. When this is the case, the detecting step may involve detecting with a luminometer, or performing luminometry. In still another embodiment, the in vitro nucleic acid amplification reaction in the amplifying step does not include an analyte-specific pair of primers that amplify the first sequence of the HIV-2 analyte nucleic acid without also being capable of amplifying the first sequence of the HIV-1 analyte nucleic acid. In yet other embodiments, the in vitro nucleic acid amplification reaction in the amplifying step can further amplify at least a first sequence of at least one analyte nucleic acid which is different from HIV-1 and HIV-2. In this instance the amplification reaction would be a "multiplex" amplification reaction. For example, in a particularly preferred embodiment of the invented method the nucleic acids of at least one of hepatitis B virus and hepatitis C virus can be amplified in the amplification reaction in addition to HIV-1 and HIV-2 nucleic acids.

A fourth aspect of the invention relates to a method of determining whether a test sample contains an HIV-1 analyte nucleic acid. The invented method involves first amplifying in a first in vitro nucleic acid amplification reaction any of a first sequence of the HIV-1 analyte nucleic acid that may be present in the test sample, and any of a first sequence of an HIV-2 analyte nucleic acid that may be present in the test sample. The first amplification reaction uses a pair of cross-reactive primers that are capable of co-amplifying HIV-1 and HIV-2 nucleic acids. Products of the first amplification reaction may include a first HIV-1 amplicon and a first HIV-2 amplicon. Next, there is a step for detecting in a single hybridization reaction any of the first HIV-1 amplicon and any of the first HIV-2 amplicon that may have been synthesized in the first amplification reaction. Detection of one of the amplicon species confirms that the test sample contains either HIV-1 or HIV-2 nucleic acids. There is next a step for amplifying in a second in vitro nucleic acid amplification reaction any of a second sequence of the HIV-1 analyte nucleic acid that maybe present in the test sample, thereby resulting in the synthesis of a second HIV-1 amplicon. Finally, there is a step for detecting the second HIV-1 amplicon using a probe that hybridizes to the second HIV-1 amplicon but not to any HIV-2 amplicon that may have been synthesized in the second amplifying step. Detection of the second HIV-1 amplicon will confirm that the test sample contains the HIV-1 analyte nucleic acid. In a preferred embodiment, the in vitro nucleic acid amplification reaction in the first amplifying step is either a TMA reaction, a NASBA reaction or a PCR reaction. When this is the case, the in vitro nucleic acid amplification reaction in the second amplifying step also can be either a TMA reaction, a NASBA reaction or a PCR reaction. In an alternative embodiment, the in vitro nucleic acid amplification reaction in the second amplifying step is either a TMA reaction, a NASBA reaction or a PCR reaction, regardless of the type of amplification reaction employed in the first amplifying step. In accordance with a different preferred embodiment, the first in vitro nucleic acid amplification reaction and the second in vitro nucleic acid amplification reaction employ different primers to synthesize the first HIV-1 amplicon and the second HIV-1 amplicon. In accordance with still a different preferred embodiment, the first and second detecting steps do not employ identical probes. However, it is preferred for the single hybridization reaction of the first amplifying step to include a cross-reactive probe which is capable of hybridizing either to the first HIV-1 amplicon or to the first HIV-2 amplicon. Still more preferably, the cross-reactive probe is labeled with a homogeneously detectable label. In certain embodiments, the homogeneously detectable label is, for example, a chemiluminescent label.

A fifth aspect of the invention relates to a method of amplifying an HIV-1 analyte nucleic acid and an HIV-2 analyte nucleic acid that may be present in a test sample. The invented method begins with a step for combining the test sample with a pair of cross-reactive primers. These primers include a cross-reactive first primer that independently hybridizes to any of a first strand of the HIV-1 analyte nucleic acid and any of a first strand of the HIV-2 analyte nucleic acid, if present in the test sample. Also included in the pair of cross-reactive primers is a cross-reactive second primer that independently hybridizes to any of a second strand of the HIV-1 analyte nucleic acid and any of a second strand of the HIV-2 analyte nucleic acid, if present in the test sample. The primers have sequences such that an extension product of the cross-reactive first primer, using as a template either the first strand of the HIV-1 analyte nucleic acid or the first strand of the HIV-2 analyte nucleic acid, hybridizes to the cross-reactive second primer. Next, there is a step for amplifying in an in vitro nucleic acid amplification reaction any of a first sequence of the HIV-1 analyte nucleic acid that may be present in the test sample and any of a first sequence of the HIV-2 analyte nucleic acid that may be present in the test sample using the pair of cross-reactive primers. This results in a first HIV-1 amplicon being synthesized if the test sample contains the HIV-1 analyte nucleic acid, and a first HIV-2 amplicon being synthesized if the test sample contains the HIV-2 analyte nucleic acid. In one embodiment, the invented method further includes a step for detecting at least one of the first HIV-1 amplicon and the first HIV-2 amplicon. In a preferred embodiment, the detecting step involves detecting both the first HIV-1 amplicon and the first HIV-2 amplicon. More preferably, the detecting step involves performing a hybridization reaction that includes a cross-reactive probe that hybridizes independently to any of the first HIV-1 amplicon and any of the first HIV-2 amplicon synthesized in the amplifying step. In another preferred embodiment, the detecting step involves detecting only the first HIV-1 amplicon and not detecting the first HIV-2 amplicon. In still another preferred embodiment, the detecting step involves detecting only the first HIV-2 amplicon and not detecting the first HIV-1 amplicon. In accordance with another preferred embodiment, when the invented method further includes a step for detecting at least one of the first HIV-1 amplicon and the first HIV-2 amplicon, it is preferred that either (a) the first sequence of the HIV-1 analyte nucleic acid is contained within the HIV-1 p31 integrase gene and the first sequence of the HIV-2 analyte nucleic acid is contained within the HIV-2 p31 integrase gene, or (b) the first sequence of the HIV-1 analyte nucleic acid is contained within the HIV-1 p51 reverse transcriptase gene and the first sequence of the HIV-2 analyte nucleic acid is contained within the HIV-2 p51 reverse transcriptase gene.

A sixth aspect of the invention relates to a composition for amplifying any of an HIV-1 or any of an HIV-2 analyte nucleic acid that may be present in a biological sample. The invented composition includes a cross-reactive first primer that independently hybridizes to any of a first strand of the HIV-1 analyte nucleic acid or any of a first strand of the HIV-2 analyte nucleic acid, if present in the biological sample. Also included in the invented composition is a cross-reactive second primer that independently hybridizes to any of a second strand of the HIV-1 analyte nucleic acid and any of a second strand of the HIV-2 analyte nucleic acid, if present in the biological sample. The cross-reactive nature of the primers means that an extension product of the cross-reactive first primer, as may be mediated by the activity of a template-dependent DNA polymerase using the first strand of either of the HIV-1 or HIV-2 analyte nucleic acid as a template, is able to hybridize to the cross-reactive second primer. In a preferred embodiment, the HIV-1 and HIV-2 analyte nucleic acids that can be amplified by the cross-reactive first and second primers encode either the viral p31 integrase or the viral p51 reverse transcriptase. Certain more preferred embodiments of the invented composition do not include a pair of HIV-2-specific primers for amplifying only the HIV-2 analyte nucleic acid without also being able to amplify the HIV-1 analyte nucleic acid, but may include a pair of HIV-1-specific primers for amplifying only the HIV-1 analyte nucleic acid without also amplifying the HIV-2 analyte nucleic acid. In accordance with still another embodiment, regardless of whether the cross-reactive first and second primers are useful for amplifying nucleic acids encoding the p31 integrase or the p51 reverse transcriptase, the invented composition may further include a pair of HIV-1-specific primers for amplifying only the HIV-1 analyte nucleic acid without also amplifying the HIV-2 analyte nucleic acid. Generally speaking, when the cross-reactive first and second primers are useful for amplifying nucleic acids encoding the p51 reverse transcriptase, the cross-reactive first primer includes a 3' terminal target-complementary sequence and optionally a cross-reactive first primer upstream sequence that is not complementary to the analyte nucleic acid sequence to be amplified. The 3' tenninal target-complementary sequence 30 of the cross-reactive first primer includes 22-28 contiguous bases contained within SEQ ID NO:60, allowing for the presence of RNA and DNA equivalent bases and nucleotide analogs. The invented composition further includes a cross-reactive second primer that includes a 3' terminal target-complementary sequence and optionally a cross-reactive second primer upstream sequence that is not complementary to the target nucleic acid sequence to be amplified. The 3' terminal target-complementary sequence of the cross-reactive second primer includes SEQ ID NO:61, allowing for the presence of RNA and DNA equivalent bases and nucleotide analogs. More preferably, the the 3' terminal target-complementary sequence of the cross-reactive first primer consists of 22-28 contiguous bases contained within SEQ ID NO:60, allowing for the presence of RNA and DNA equivalent bases and nucleotide analogs, and the 3' terminal target-complementary sequence of the cross-reactive second primer consists of SEQ ID NO:61, allowing for the presence of RNA and DNA equivalent bases and nucleotide analogs. In certain preferred embodiments, the first primer and the second primer are each up to 60 bases in length. In certain other preferred embodiments, the first primer does not include the optional first primer upstream sequence, the first primer being up to 28 bases in length, and the second primer is up to 60 bases in length. In still other preferred embodiments, the first primer is up to 60 bases in length, and the second primer does not include the optional second primer upstream sequence, the second primer being 26 bases in length. In yet still other preferred embodiments, the first primer does not include the optional first primer upstream sequence, the first primer being up to 28 bases in length, and the second primer does not include the optional second primer upstream sequence, the second primer being 26 bases in length. When this is the case, meaning that the first primer is up to 28 bases in length and the second primer is 26 bases in length, there are certain preferred combinations of primers that can be used in the invented combination. In a first preferred combination, the 3' terminal target-complementary sequence of the first primer is SEQ ID NO:51, and the 3' terminal target-complementary sequence of the second primer is any of SEQ ID NO:47, SEQ ID NO:49 and SEQ ID NO:50. In a second preferred combination, the 3' terminal target-complementary sequence of the first primer is SEQ ID NO:52, and the 3' terminal target-complementary sequence of the second primer is SEQ ID NO:48. In a third preferred combination, the 3' terminal target-complementary sequence of the first primer is SEQ ID NO:53 and the 3' terminal target-complementary sequence of the second primer is any of SEQ ID NO:47, SEQ ID NO:49 and SEQ ID NO:50. In a fourth preferred combination, the 3' terminal target-complementary sequence of the first primer is SEQ ID NO:54, and the 3' terminal target-complementary sequence of the second primer is SEQ ID NO:48. In a different embodiment, when the first primer and the second primer are each up to 60 bases in length, the 3' terminal target-complementary sequence of the first primer is any of SEQ ID Nos:51-54. More preferrably, the 3' terminal target-complementary sequence of the second primer is any of SEQ ID Nos:47-50. In still a different preferred embodiment, when the first primer is up to 60 bases in length, and when the second primer does not include the optional second primer upstream sequence, the second primer being 26 bases in length, the 3' terminal target-complementary sequence of the second primer is any of SEQ ID Nos:47-50. More preferably, the first primer includes the optional first primer upstream sequence, and the 3' terminal target-complementary sequence of the first primer is any of SEQ ID NO:51-54. When this is the case, there are certain preferred combinations of primers that can be used in the invented combination. In a first preferred combination, the 3' terminal target-complementary sequence of the first primer is SEQ ID NO:51, and the 3' terminal target-complementary sequence of the second primer is any of SEQ ID NO:47, SEQ ID NO:49 and SEQ ID NO:50. In a second preferred combination, the 3' terminal target-complementary sequence of the first primer is SEQ ID NO:52, and the 3' terminal target-complementary sequence of the second primer is SEQ ID NO:48. In a third preferred combination, the 3' terminal target-complementary sequence of the first primer is SEQ ID NO:53, and the 3' terminal target-complementary sequence of the second primer is any of SEQ ID NO:47, SEQ ID NO:49 and SEQ ID NO:50. In a fourth preferred combination, the 3' terminal target-complementary sequence of the first primer is SEQ ID NO:54, and the 3' terminal target-complementary sequence of the second primer is SEQ ID NO:48. Again generally speaking, when the cross-reactive first and second primers are useful for amplifying nucleic acids encoding the p31 integrase, the cross-reactive first primer includes a 3' terminal target-complementary sequence and optionally a cross-reactive first primer upstream sequence that is not complementary to the analyte nucleic acid sequence to be amplified. The 3' terminal target-complementary sequence of the cross-reactive first primer consists of any of SEQ ID NOs: 13-15. The invented composition further includes a cross-reactive second primer that includes a 3' terminal target-complementary sequence and optionally a cross-reactive second primer upstream sequence that is not complementary to the target nucleic acid sequence to be amplified. The 3' terminal target-complementary sequence of the cross-reactive second primer includes the sequence ACARYAG-TACWAATGGC (SEQ ID NO:10), allowing for the substitution of up to two base analogs. In a preferred embodiment, the cross-reactive first primer and the cross-reactive second primer are each up to 75 bases in length. More preferably, the 3' terminal target-complementary sequence of the cross-reactive second primer is any of SEQ ID NO:2, SEQ ID NO:7, SEQ ID NO:8 and SEQ ID NO:9. Still more preferably, the cross-reactive first primer is SEQ ID NO:14, and the cross-reactive second primer is any of SEQ ID NO:2, SEQ ID NO:7, SEQ ID NO:8 and SEQ ID NO:9. In accordance with yet more preferred embodiments, either the cross-reactive first primer is SEQ ID NO:14, and the cross-reactive second primer is SEQ ID NO:7, or the cross-reactive first primer is SEQ ID NO:14, and the cross-reactive second primer is SEQ ID NO:2.

A seventh aspect of the invention relates to a probe for detecting an HIV-1 or an HIV-2 nucleic acid. The invented probe includes a probe sequence that consists of a target-complementary sequence of bases, and optionally one or more base sequences that are not complementary to the nucleic acids that are to be detected. The target-complementary sequence of bases can be of any of: (a) SEQ ID NO:42 or the complement thereof, allowing for the presence of RNA and DNA equivalent bases; (b) SEQ ID NO:43 or the complement thereof, allowing for the presence of RNA and DNA equivalent bases; or (c) SEQ ID NO:44 or the complement thereof, allowing for the presence of RNA and DNA equivalent bases. In all instances the hybridization probe has a length of up to 60 bases. In a preferred embodiment, the probe further includes a detectable label. For example, the detectable label can be a chemiluminescent label. In accordance with a different embodiment, the length of the hybridization probe is up to 26 bases. In accordance with still a different embodiment, the probe does not include the optional one or more base sequences that are not complementary to the nucleic acids that are to be detected, and the probe sequence is any of SEQ ID NO:42 or the complement thereof, SEQ ID NO:43 or the complement thereof, and SEQ ID NO:44 or the complement thereof.

An eighth aspect of the invention relates to another probe for detecting an HIV-1 or an HIV-2 nucleic acid. The invented probe includes a probe sequence that consists of a target-complementary sequence of bases, and optionally one or more base sequences that are not complementary to the nucleic acid that is to be detected. The target-complementary sequence of bases may be any of SEQ ID Nos:23-36.

DEFINITIONS

The following terms have the following meanings for the purpose of this disclosure, unless expressly stated to the contrary herein.

As used herein, a "biological sample" is any tissue or polynucleotide-containing material obtained from a human, animal or environmental sample. Biological samples in accordance with the invention include peripheral blood, plasma, serum or other body fluid, bone marrow or other organ, biopsy tissues or other materials of biological origin. A biological sample may be treated to disrupt tissue or cell structure, thereby releasing intracellular components into a solution which may contain enzymes, buffers, salts, detergents and the like.

As used herein, "polynucleotide" means either RNA or DNA, along with any synthetic nucleotide analogs or other molecules that may be present in the sequence and that do not prevent hybridization of the polynucleotide with a second molecule having a complementary sequence.

As used herein, a "detectable label" is a chemical species that can be detected or can lead to a detectable response. Detectable labels in accordance with the invention can be linked to polynucleotide probes either directly or indirectly, and include radioisotopes, enzymes, haptens, chromophores such as dyes or particles that impart a detectable color (e.g., latex beads or metal particles), luminescent compounds (e.g., bioluminescent, phosphorescent or chemiluminescent moieties) and fluorescent compounds.

A "homogeneous detectable label" refers to a label that can be detected in a homogeneous fashion by determining whether the label is on a probe hybridized to a target sequence. That is, homogeneous detectable labels can be detected without physically removing hybridized from unhybridized forms of the label or labeled probe. Homogeneous detectable labels are preferred when using labeled probes for detecting either HIV-1 or HIV-2 nucleic acids. Examples of homogeneous labels include fluorescent labels, such as those associated with molecular beacons, and chemiluminescent labels such as those detailed by Arnold et al., U.S. Pat. No. 5,283,174; Woodhead et al., U.S. Pat. No. 5,656,207; and Nelson et al., U.S. Pat. No. 5,658,737. Preferred labels for use in homogenous assays include chemiluminescent compounds (e.g., see Woodhead et al., U.S. Pat. No. 5,656,207; Nelson et al., U.S. Pat. No. 5,658,737; and Arnold, Jr., et al., U.S. Pat. No. 5,639,604). Preferred chemiluminescent labels are acridinium ester ("AE") compounds, such as standard AE or derivatives thereof (e.g., naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy(cinnamyl)-AE, ortho-methyl-AE, ortho-fluoro-AE, 1- or 3-methyl-ortho-fluoro-AE, 1- or 3-methyl-meta-difluoro-AE, and 2-methyl-AE).

A "homogeneous assay" refers to a detection procedure that does not require physical separation of hybridized probe from non-hybridized probe prior to determining the extent of specific probe hybridization. Exemplary homogeneous assays, such as those described herein, can employ molecular beacons or other self-reporting probes which emit fluorescent signals when hybridized to an appropriate target, chemiluminescent acridinium ester labels which can be selectively destroyed by chemical means unless present in a hybrid duplex, and other homogeneously detectable labels that will be familiar to those having an ordinary level of skill in the art.

As used herein, "amplification" refers to an in vitro procedure for obtaining multiple copies of a target nucleic acid sequence, its complement or fragments thereof.

By "target nucleic acid" or "target" is meant a nucleic acid containing a target nucleic acid sequence. In general, a target nucleic acid sequence that is to be amplified will be positioned between two oppositely disposed primers, and will include the portion of the target nucleic acid that is fully complementary to each of the primers.

By "target nucleic acid sequence" or "target sequence" or "target region" is meant a specific deoxyribonucleotide or ribonucleotide sequence comprising all or part of the nucleotide sequence of a single-stranded nucleic acid molecule, and the deoxyribonucleotide or ribonucleotide sequence complementary thereto.

By "transcription associated amplification" is meant any type of nucleic acid amplification that uses an RNA polymerase to produce multiple RNA transcripts from a nucleic acid template. One example of a transcription associated amplification method, called "Transcription Mediated Amplification" (TMA), generally employs an RNA polymerase, a DNA polymerase, deoxyribonucleoside triphosphates, ribonucleoside triphosphates, and a promoter-template complementary oligonucleotide, and optionally may include one or more analogous oligonucleotides. Variations of TMA are well known in the art as disclosed in detail in Burg et al., U.S. Pat. No. 5,437,990; Kacian et al., U.S. Pat. Nos. 5,399,491 and 5,554,516; Kacian et al., PCT No. WO 93/22461; Gingeras et al., PCT No. WO 88/01302; Gingeras et al., PCT No. WO 88/10315; Malek et al., U.S. Pat. No. 5,130,238; Urdea et al., U.S. Pat. Nos. 4,868,105 and 5,124,246; McDonough et al., PCT No. WO 94/03472; and Ryder et al., PCT No. WO 95/03430. The methods of Kacian et al. are preferred for conducting nucleic acid amplification procedures of the type disclosed herein.

As used herein, an "oligonucleotide" or "oligomer" is a polymeric chain of at least two, generally between about five and about 100, chemical subunits, each subunit comprising a nucleotide base moiety, a sugar moiety, and a linking moiety that joins the subunits in a linear spacial configuration. Common nucleotide base moieties are guanine (G), adenine (A), cytosine (C), thymine (T) and uracil (U), although other rare or modified nucleotide bases able to hydrogen bond are well known to those skilled in the art. Oligonucleotides may optionally include analogs of any of the sugar moieties, the base moieties, and the backbone constituents. Preferred oligonucleotides of the present invention fall in a size range of about 10 to about 100 residues. Oligonucleotides may be purified from naturally occurring sources, but preferably are synthesized using any of a variety of well known enzymatic or chemical methods.

As used herein, a "probe" is an oligonucleotide that hybridizes specifically to a target sequence in a nucleic acid, preferably in an amplified nucleic acid, under conditions that promote hybridization, to form a detectable hybrid. A probe optionally may contain a detectable moiety which either may be attached to the end(s) of the probe or may be internal. The nucleotides of the probe which combine with the target polynucleotide need not be strictly contiguous, as may be the case with a detectable moiety internal to the sequence of the probe. Detection may either be direct (i.e., resulting from a probe hybridizing directly to the target sequence or amplified nucleic acid) or indirect (i.e., resulting from a probe hybridizing to an intermediate molecular structure that links the probe to the target sequence or amplified nucleic acid). The "target" of a probe generally refers to a sequence contained within an amplified nucleic acid sequence which hybridizes specifically to at least a portion of a probe oligonucleotide using standard hydrogen bonding (i.e., base pairing). A probe may comprise target-specific sequences and optionally other sequences that are non-complementary to the target sequence that is to be detected. These non-complementary sequences may comprise a promoter sequence, a restriction endonuclease recognition site, or sequences that contribute to three-dimensional conformation of the probe (e.g., as described in Lizardi et al., U.S. Pat. Nos. 5,118,801 and 5,312,728). Sequences that are "sufficiently complementary" allow stable hybridization of a probe oligonucleotide to a target sequence that is not completely complementary to the probe's target-specific sequence.

As used herein, an "amplification primer" is an oligonucleotide that hybridizes to a target nucleic acid, or its complement, and participates in a nucleic acid amplification reaction. For example, amplification primers, or more simply "primers," may be optionally modified oligonucleotides which are capable of hybridizing to a template nucleic acid and may have a 3' end that can be extended by a DNA polymerase activity. In general, a primer will have a downstream sequence capable of hybridizing to a target nucleic acid, and optionally an upstream sequence that is not complementary to the target nucleic acid. The optional upstream sequence may, for example, serve as an RNA polymerase promoter or contain restriction endonuclease cleavage sites.

As used herein, and with reference to oligonucleotide probes or primers, the term "cross-react" or "cross-reactive" or variants thereof means that the probes or primers are not strictly specific for a single species of target polynucleotide. A probe that hybridizes to HIV-1 nucleic acids but not to HIV-2 nucleic acids cannot be said to be cross-reactive. Conversely, a probe that is able to hybridize to both HIV-1 and HIV-2 target nucleic acids to form detectable hybridization complexes would be considered "cross-reactive." Similarly, cross-reactive primers are capable of participating in a nucleic acid amplification reaction using either HIV-1 or HIV-2 nucleic acids as templates to result in the synthesis of HIV-1 amplicons and HIV-2 amplicons.

By "substantially homologous," "substantially corresponding" or "substantially corresponds" is meant that the subject oligonucleotide has a base sequence containing an at least 10 contiguous base region that is at least 70% homologous, preferably at least 80% homologous, more preferably at least 90% homologous, and most preferably 100% homologous to an at least 10 contiguous base region present in a reference base sequence (excluding RNA and DNA equivalents). Those skilled in the art will readily appreciate modifications that could be made to the hybridization assay conditions at various percentages of homology to permit hybridization of the oligonucleotide to the target sequence while preventing unacceptable levels of non-specific hybridization. The degree of similarity is determined by comparing the order of nucleobases making up the two sequences and does not take into consideration other structural differences which may exist between the two sequences, provided the structural differences do not prevent hydrogen bonding with complementary bases. The degree of homology between two sequences can also be expressed in terms of the number of base mismatches present in each set of at least 10 contiguous bases being compared, which may range from 0-2 base differences.

By "substantially complementary" is meant that the subject oligonucleotide has a base sequence containing an at least 10 contiguous base region that is at least 70% complementary, preferably at least 80% complementary, more preferably at least 90% complementary, and most preferably 100% complementary to an at least 10 contiguous base region present in a target nucleic acid sequence (excluding RNA and DNA equivalents). (Those skilled in the art will readily appreciate modifications that could be made to the hybridization assay conditions at various percentages of complementarity to permit hybridization of the oligonucleotide to the target sequence while preventing unacceptable levels of non-specific hybridization.) The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 10 contiguous bases being compared, which may range from 0-2 base mismatches.

By "sufficiently complementary" is meant a contiguous nucleic acid base sequence that is capable of hybridizing to another base sequence by hydrogen bonding between a series of complementary bases. Complementary base sequences may be complementary at each position in the base sequence of an oligonucleotide using standard base pairing (e.g., G:C, A:T or A:U pairing) or may contain one or more residues that are not complementary using standard hydrogen bonding (including abasic "nucleotides"), but in which the entire complementary base sequence is capable of specifically hybridizing with another base sequence under appropriate hybridization conditions. Contiguous bases are preferably at least about 80%, more preferably at least about 90%, and most preferably about 100% complementary to a sequence to which an oligonucleotide is intended to specifically hybridize. Appropriate hybridization conditions are well known to those skilled in the art, can be predicted readily based on base sequence composition, or can be determined empirically by using routine testing (e.g., See Sambrook et al., *Molecular Cloning, A Laboratory Manual*, $2^{nd}$ ed. (Cold Spring Harbor Laboratory Press, Cold Spring Harbor, N.Y., 1989) at §§ 1.90-1.91, 7.37-7.57, 9.47-9.51 and 11.47-11.57 particularly at §§ 9.50-9.51, 11.12-11.13, 11.45-11.47 and 11.55-11.57).

By "capture oligonucleotide" is meant at least one nucleic acid oligonucleotide that provides means for specifically joining a target sequence and an immobilized oligonucleotide due to base pair hybridization. A capture oligonucleotide preferably includes two binding regions: a target sequence-binding region and an immobilized probe-binding region, usually contiguous on the same oligonucleotide, although the capture oligonucleotide may include a target sequence-binding region and an immobilized probe-binding region which are present on two different oligonucleotides joined together by one or more linkers. For example, an immobilized probe-binding region may be present on a first oligonucleotide, the target sequence-binding region may be present on a second oligonucleotide, and the two different oligonucleotides are joined by hydrogen bonding with a linker that is a third oligonucleotide containing sequences that hybridize specifically to the sequences of the first and second oligonucleotides.

By "immobilized probe" or "immobilized nucleic acid" is meant a nucleic acid that joins, directly or indirectly, a capture oligonucleotide to an immobilized support. An immobilized probe is an oligonucleotide joined to a solid support that facilitates separation of bound target sequence from unbound material in a sample.

By "separating" or "purifying" is meant that one or more components of the biological sample are removed from one or more other components of the sample. Sample components include nucleic acids in a generally aqueous solution phase which may also include materials such as proteins, carbohydrates, lipids and labeled probes. Preferably, the separating or purifying step removes at least about 70%, more preferably at least about 90% and, even more preferably, at least about 95% of the other components present in the sample.

By "RNA and DNA equivalents" or "RNA and DNA equivalent bases" is meant molecules, such as RNA and DNA, having the same complementary base pair hybridization properties. RNA and DNA equivalents have different sugar moieties (i.e., ribose versus deoxyribose) and may differ by the presence of uracil in RNA and thymine in DNA. The differences between RNA and DNA equivalents do not contribute to differences in homology because the equivalents have the same degree of complementarity to a particular sequence.

By "consisting essentially of" is meant that additional component(s), composition(s) or method step(s) that do not materially change the basic and novel characteristics of the present invention may be included in the compositions or kits or methods of the present invention. Such characteristics include the ability to selectively detect HIV-1, HIV-2, or the combination of HIV-1 and HIV-2 nucleic acids in biological samples such as whole blood or plasma. Any component(s), composition(s), or method step(s) that have a material effect on the basic and novel characteristics of the present invention would fall outside of this term.

DETAILED DESCRIPTION OF THE INVENTION

Figure 1:
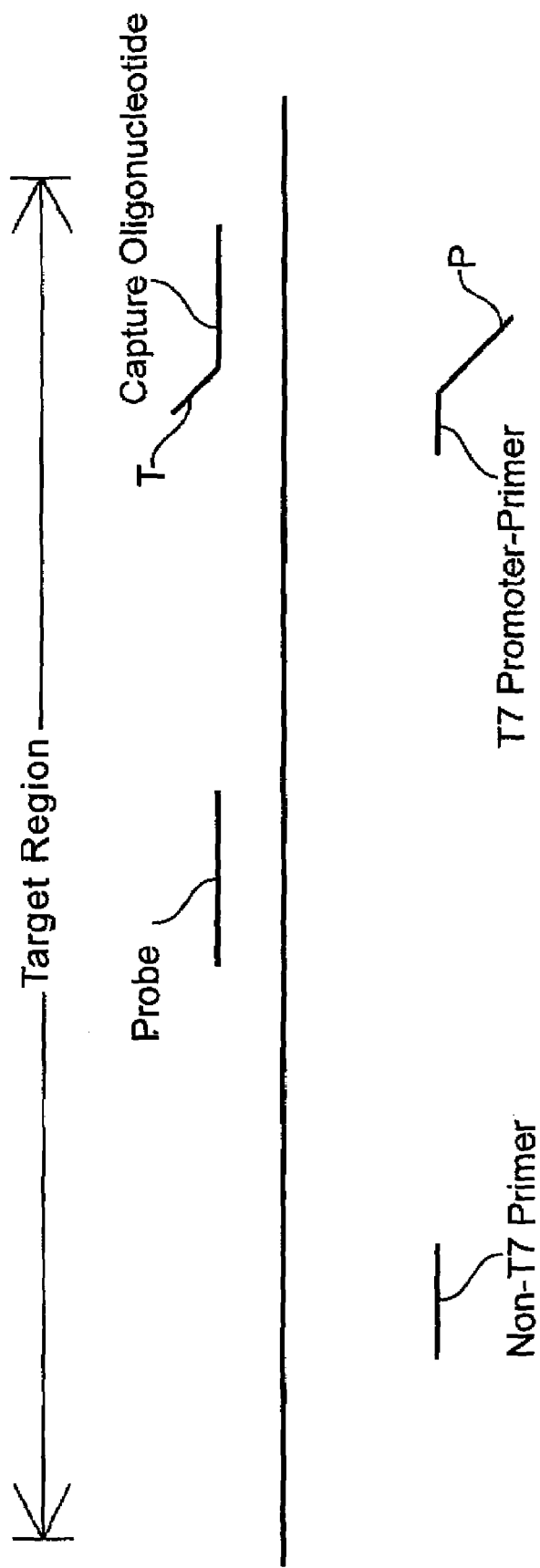
FIG. 1 is a schematic diagram illustrating the various polynucleotides that can be used for detecting a target region within the nucleic acid of HIV-1 or HIV-2 (represented by a thick horizontal line). Positions of the following nucleic acids arc shown relative to the target region: "Capture Oligonucleotide" refers to the nucleic acid used to hybridize to and capture the target nucleic acid prior to amplification, where "T" refers to a tail sequence used to hybridize an immobilized oligonucleotide having a complementary sequence (not shown); "Non-T7 Primer" and "T7 Promoter-Primer" represent two amplification primers used for conducting TMA, where "P" indicates the promoter sequence of the T7 promoter-primer; and "Probe" refers to the probe used for detecting amplified nucleic acid.

Disclosed herein are compositions, methods and kits for detecting the nucleic acids of HIV-1, HIV-2, br the combination of HIV-1 and HIV-2 in biological samples such as blood, serum, plasma or other body fluid or tissue. The probes, primers and methods of the invention can be used either in diagnostic applications or for screening donated blood and blood products or other tissues that may contain infectious particles.

Introduction and Overview

The present invention includes compositions (i.e., amplification oligonucleotides or primers, and probes), methods and kits that are particularly useful for detecting the nucleic acids of HIV-1, HIV-2, or the combination of HIV-1 and HIV-2 in a biological sample. To design oligonucleotide sequences appropriate for such uses, known HIV-1 and HIV-2 nucleic acid sequences were first compared to identify candidate regions of the viral genomes that could serve as reagents in a diagnostic assay. As a result of these comparisons, particular sequences were selected and tested as targets for detection using the capture oligonucleotides, primers and probes shown schematically in FIG. 1. Portions of sequences containing relatively few variants were chosen as starting points for designing synthetic oligonucleotides suitable for use in capture, amplification and detection of amplified sequences.

Based on these analyses, the amplification primer and probe sequences presented below were designed. Those having an ordinary level of skill in the art will appreciate that any primer sequences specific for HIV-1, HIV-2, or the combination of HIV-1 and HIV-2 targets, with or without a T7 promoter sequence, may be used as primers in the various primer-based in vitro amplification methods described below. It is also contemplated that oligonucleotides having the sequences disclosed herein could serve alternative functions in assays for detecting HIV-1 and/or HIV-2 nucleic acids. For example, the capture oligonucleotides disclosed herein could serve as hybridization probes, the hybridization probes disclosed herein could be used as amplification primers, and the amplification primers disclosed herein could be used as hybridization probes in alternative detection assays.

The amplification primers disclosed herein are particularly contemplated as components of multiplex amplification reactions wherein several amplicon species can be produced from an assortment of target-specific primers. For example, it is contemplated that certain preferred primers disclosed herein can be used in multiplex amplification reactions that are capable of amplifying polynucleotides of unrelated viruses without substantially compromising the sensitivities of those assays. Particular examples of these unrelated viruses include HCV and HBV.

Useful Amplification Methods

Amplification methods useful in connection with the present invention include: Transcription Mediated Amplification (TMA), Nucleic Acid Sequence-Based Amplification (NASBA), the Polymerase Chain Reaction (PCR), Strand Displacement Amplification (SDA), and amplification methods using self-replicating polynucleotide molecules and replication enzymes such as MDV-1 RNA and Q-beta enzyme. Methods for carrying out these various amplification techniques respectively can be found in U.S. Pat. No. 5,399,491, published European patent application EP 0 525 882, U.S. Pat. No. 4,965,188, U.S. Pat. No. 5,455,166, U.S. Pat. No. 5,472,840 and Lizardi et al., *BioTechnology* 6:1197 (1988). The disclosures of these documents which describe how to perform nucleic acid amplification reactions are hereby incorporated by reference.

In a highly preferred embodiment of the invention, analyte nucleic acid sequences are amplified using a TMA protocol. According to this protocol, the reverse transcriptase which provides the DNA polymerase activity also possesses an endogenous RNase H activity. One of the primers used in this procedure contains a promoter sequence positioned upstream of a sequence that is complementary to one strand of a target nucleic acid that is to be amplified. In the first step of the amplification, a promoter-primer hybridizes to the target RNA at a defined site, Reverse transcriptase creates a complementary DNA copy of the target RNA by extension from the 3' end of the promoter-primer. Following interaction of an opposite strand primer with the newly synthesized DNA strand, a second strand of DNA is synthesized from the end of the primer by reverse transcriptase, thereby creating a double-stranded DNA molecule. RNA polymerase recognizes the promoter sequence in this double-stranded DNA template and initiates transcription. Each of the newly synthesized RNA amplicons re-enters the TMA process and serves as a template for a new round of replication, thereby leading to an exponential expansion of the RNA amplicon. Since each of the DNA templates can make 100-1000 copies of RNA amplicon, this expansion can result in the production of 10 billion amplicons in less than one hour. The entire process is autocatalytic and is performed at a constant temperature.

Structural Features of Primers

As indicated above, a "primer" refers to an optionally modified oligonucleotide which is capable of participating in a nucleic acid amplification reaction. Highly preferred primers are capable of hybridizing to a template nucleic acid and have a 3' end that can be extended by a DNA polymerase activity. The 5' region of the primer may be non-complementary to the target nucleic acid. If the 5' non-complementary region includes a promoter sequence, it is referred to as a "promoter-primer." Those skilled in the art will appreciate that any oligonucleotide that can function as a primer (i.e., an oligonucleotide that hybridizes specifically to a target sequence and has a 3' end capable of extension by a DNA polymerase activity) can be modified to include a 5' promoter sequence, and thus could function as a promoter-primer. Similarly, any promoter-primer can be modified by removal of, or synthesis without, a promoter sequence and still function as a primer.

Nucleotide base moieties of primers may be modified (e.g., by the addition of propyne groups), as long as the modified base moiety retains the ability to form a non-covalent association with G, A, C, T or U, and as long as an oligonucleotide comprising at least one modified nucleotide base moiety or analog is not sterically prevented from hybridizing with a single-stranded nucleic acid. As indicated below in connection with the chemical composition of useful probes, the nitrogenous bases of primers in accordance with the invention may be conventional bases (A, G, C, T, U), known analogs thereof (e.g., inosine or "I" having hypoxanthine as its base moiety; see *The Biochemistry of the Nucleic Acids* 5-36, Adams et al., ed., 11$^{th}$ ed., 1992), known derivatives of purine or pyrimidine bases (e.g., N$^4$-methyl deoxygaunosine, deaza- or aza-purines and deaza- or aza-pyrimidines, pyrimidine bases having substituent groups at the 5 or 6 position, purine bases having an altered or a replacement substituent at the 2, 6 or 8 positions, 2-amino-6-methylaminopurine, O$^6$-methylguanine, 4-thio-pyrimidines, 4-amino-pyrimidines, 4-dimethylhydrazine-pyrimidines, and O$^4$-alkyl-pyrimidines (see, Cook, PCT Int'l Pub. No. WO 93/13121) and "abasic" residues where the backbone includes no nitrogenous base for one or more residues of the polymer (see Arnold et al., U.S. Pat. No. 5,585,481). Common sugar moieties that comprise the primer backbone include ribose and deoxyribose, although 2'-O-methyl ribose (OMe), halogenated sugars, and other modified sugar moieties may also be used. Usually, the linking group of the primer backbone is a phosphorus-containing moiety, most commonly a phosphodiester linkage, although other linkages, such as, for example, phosphorothioates, methylphosphonates, and non-phosphorus-containing linkages such as peptide-like linkages found in "peptide nucleic acids" (PNA) also are intended for use in the assay disclosed herein.

Useful Probe Labeling Systems and Detectable Moieties

Essentially any labeling and detection system that can be used for monitoring specific nucleic acid hybridization can be used in conjunction with the present invention. Included among the collection of useful labels are radiolabels, enzymes, haptens, linked oligonucleotides, chemiluminescent molecules, fluorescent moieties (either alone or in combination with "quencher" moieties), and redox-active moieties that are amenable to electronic detection methods. Preferred chemiluminescent molecules include acridinium esters of the type disclosed by Arnold et al., in U.S. Pat. No. 5,283,174 for use in connection with homogenous protection assays, and of the type disclosed by Woodhead et al., in U.S. Pat. No. 5,656,207 for use in connection with assays that quantify multiple targets in a single reaction. The disclosures contained in these patent documents are hereby incorporated by reference. Preferred electronic labeling and detection approaches are disclosed in U.S. Pat. Nos. 5,591,578 and 5,770,369, and the published international patent application WO 98/57158, the disclosures of which are hereby incorporated by reference. Redox active moieties useful as labels in the present invention include transition metals such as Cd, Mg, Cu, Co, Pd, Zn, Fe and Ru.

Particularly preferred detectable labels for probes in accordance with the present invention are detectable in homogeneous assay systems (i.e., where, in a mixture, bound labeled probe exhibits a detectable change, such as stability or differential degradation, compared to unbound labeled probe). While other homogeneously detectable labels, such as fluorescent labels and electronically detectable labels, are intended for use in the practice of the present invention, a preferred label for use in homogenous assays is a chemiluminescent compound (e.g., as described by Woodhead et al., in U.S. Pat. No. 5,656,207; by Nelson et al., in U.S. Pat. No. 5,658,737; or by Arnold et al., in U.S. Pat. No. 5,639,604). Particularly preferred chemiluminescent labels include acridinium ester ("AE") compounds, such as standard AE or derivatives thereof, such as naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy(cinnamyl)-AE, ortho-methyl-AE, ortho-fluoro-AE, 1- or 3-methyl-ortho-fluoro-AE, 1- or 3-methyl-meta-difluoro-AE, and 2-methyl-AE.

In some applications, probes exhibiting at least some degree of self-complementarity are desirable to facilitate detection of probe:target duplexes in a test sample without first requiring the removal of unhybridized probe prior to detection. By way of example, structures referred to as "molecular torches" are designed to include distinct regions of self-complementarity (coined "the target binding domain" and "the target closing domain") which are connected by a joining region and which hybridize to one another under predetermined hybridization assay conditions. When exposed to denaturing conditions, the two complementary regions (which may be fully or partially complementary) of the molecular torch melt, leaving the target binding domain available for hybridization to a target sequence when the predetermined hybridization assay conditions are restored. Molecular torches are designed so that the target binding domain favors hybridization to the target sequence over the target closing domain. The target binding domain and the target closing domain of a molecular torch include interacting labels (e.g., fluorescent/quencher) positioned so that a different signal is produced when the molecular torch is self-hybridized as opposed to when the molecular torch is hybridized to a target nucleic acid, thereby permitting detection of probe:target duplexes in a test sample in the presence of unhybridized probe having a viable label associated therewith. Molecular torches are fully described in U.S. Pat. No. 6,361,945, the disclosure of which is hereby incorporated by reference.

Another example of a self-complementary hybridization assay probe that may be used in conjunction with the invention is a structure commonly referred to as a "molecular beacon." Molecular beacons comprise nucleic acid molecules having a target complementary sequence, an affinity pair (or nucleic acid arms) holding the probe in a closed conformation in the absence of a target nucleic acid sequence, and a label pair that interacts when the probe is in a closed conformation. Hybridization of the target nucleic acid and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are fully described in U.S. Pat. No. 5,925,517, the disclosure of which is hereby incorporated by reference. Molecular beacons useful for detecting specific nucleic acid sequences may be created by appending to either end of one of the probe sequences disclosed herein, a first nucleic acid arm comprising a fluorophore and a second nucleic acid arm comprising a quencher moiety. In this configuration, the probe sequence disclosed herein serves as the target-complementary "loop" portion of the resulting molecular beacon.

Molecular beacons preferably are labeled with an interactive pair of detectable labels. Examples of detectable labels that are preferred as members of an interactive pair of labels interact with each other by FRET or non-FRET energy transfer mechanisms. Fluorescence resonance energy transfer (FRET) involves the radiationless transmission of energy quanta from the site of absorption to the site of its utilization in the molecule, or system of molecules, by resonance interaction between chromophores, over distances considerably greater than interatomic distances, without conversion to thermal energy, and without the donor and acceptor coming into kinetic collision. The "donor" is the moiety that initially absorbs the energy, and the "acceptor" is the moiety to which the energy is subsequently transferred. In addition to FRET, there are at least three other "non-FRET" energy transfer processes by which excitation energy can be transferred from a donor to an acceptor molecule.

When two labels are held sufficiently close that energy emitted by one label can be received or absorbed by the second label, whether by a FRET or non-FRET mechanism, the two labels are said to be in "energy transfer relationship" with each other. This is the case, for example, when a molecular beacon is maintained in the closed state by formation of a stem duplex, and fluorescent emission from a fluorophore attached to one arm of the probe is quenched by a quencher moiety on the opposite arm.

Highly preferred label moieties for molecular beacons include a fluorophore and a second moiety having fluorescence quenching properties (i.e., a "quencher"). In this embodiment, the characteristic signal is likely fluorescence of a particular wavelength, but alternatively could be a visible light signal. When fluorescence is involved, changes in emission are preferably due to FRET, or to radiative energy transfer or non-FRET modes. When a molecular beacon having a pair of interactive labels in the closed state is stimulated by an appropriate frequency of light, a fluorescent signal is generated at a first level, which may be very low. When this same probe is in the open state and is stimulated by an appropriate frequency of light, the fluorophore and the quencher moieties are sufficiently separated from each other that energy transfer between them is substantially precluded. Under that condition, the quencher moiety is unable to quench the fluorescence from the fluorophore moiety. If the fluorophore is stimulated by light energy of an appropriate wavelength, a fluorescent signal of a second level, higher than the first level, will be generated. The difference between the two levels of fluorescence is detectable and measurable. Using fluorophore and quencher moieties in this manner, the molecular beacon is only "on" in the "open" conformation and indicates that the probe is bound to the target by emanating an easily detectable signal. The conformational state of the probe alters the signal generated from the probe by regulating the interaction between the label moieties.

Examples of donor/acceptor label pairs that may be used in connection with the invention, making no attempt to distinguish FRET from non-FRET pairs, include fluorescein/tetramethylrhodamine, IAEDANS/fluororescein, EDANS/DABCYL, coumarin/DABCYL, fluorescein/fluorescein, BODIPY FL/BODIPY FL, fluorescein/DABCYL, lucifer yellow/DABCYL, BODIPY/DABCYL, eosine/DABCYL, erythrosine/DABCYL, tetramethylrhodamine/DABCYL, Texas Red/DABCYL, CY5/BH1, CY5/BH2, CY3/BH1, CY3/BH2 and fluorescein/QSY7 dye. Those having an ordinary level of skill in the art will understand that when donor and acceptor dyes are different, energy transfer can be detected by the appearance of sensitized fluorescence of the acceptor or by quenching of donor fluorescence. When the donor and acceptor species are the same, energy can be detected by the resulting fluorescence depolarization. Non-fluorescent acceptors such as DABCYL and the QSY 7 dyes advantageously eliminate the potential problem of background fluorescence resulting from direct (i.e., non-sensitized) acceptor excitation. Preferred fluorophore moieties that can be used as one member of a donor-acceptor pair include fluorescein, ROX, and the CY dyes (such as CY5). Highly preferred quencher moieties that can be used as another member of a donor-acceptor pair include DABCYL and the BLACK HOLE QUENCHER moieties which are available from Biosearch Technologies, Inc., (Novato, Calif.).

Synthetic techniques and methods of bonding labels to nucleic acids and detecting labels are well known in the art (e.g., see Sambrook et al., *Molecular Cloning, A Laboratory Manual*, $2^{nd}$ ed. (Cold Spring Harbor Laboratory Press, Cold Spring Harbor, N.Y., 1989), Chapter 10; Nelson et al., U.S. Pat. No. 5,658,737; Woodhead et al., U.S. Pat. No. 5,656,207; Hogan et al., U.S. Pat. No. 5,547,842; Arnold et al., U.S. Pat. No. 5,283,174; Kourilsky et al., U.S. Pat. No. 4,581,333), and Becker et al., European Patent App. No. 0 747 706.

Chemical Composition of Probes

Probes in accordance with the invention comprise polynucleotides or polynucleotide analogs and optionally may carry a detectable label covalently bonded thereto. Nucleosides or nucleoside analogs of the probe comprise nitrogenous heterocyclic bases, or base analogs, where the nucleosides are linked together, for example by phospohdiester bonds to form a polynucleotide. Accordingly, a probe may comprise conventional ribonucleic acid (RNA) and/or deoxyribonucleic acid (DNA), but also may comprise chemical analogs of these molecules. The "backbone" of a probe may be made up of a variety of linkages known in the art, including one or more sugar-phosphodiester linkages, peptide-nucleic acid bonds (sometimes referred to as "peptide nucleic acids" as described by Hyldig-Nielsen et al., PCT Int'l Pub. No. WO 95/32305), phosphorothioate linkages, methylphosphonate linkages or combinations thereof. Sugar moieties of the probe may be either ribose or deoxyribose, or similar compounds having known substitutions, such as, for example, 2'-O-methyl ribose and 2' halide substitutions (e.g., 2'-F). The nitrogenous bases may be conventional bases (A, G, C, T, U), known analogs thereof (e.g., inosine or "I"; see *The Biochemistry of the Nucleic Acids* 5-36, Adams et al., ed., 11$^{th}$ ed., 1992), known derivatives of purine or pyrimidine bases (e.g., $N^4$-methyl deoxygaunosine, deaza- or aza-purines and deaza- or aza-pyrimidines, pyrimidine bases having substituent groups at the 5 or 6 position, purine bases having an altered or a replacement substituent at the 2, 6 or 8 positions, 2-amino-6-methylaminopurine, $O^6$-methylguanine, 4-thio-pyrimidines, 4-amiino-pyrimidines, 4-dimethylhydrazine-pyrimidines, and $O^4$-alkyl-pyrimidines (see, Cook, PCT Int'l Pub. No. WO 93/13121) and "abasic" residues where the backbone includes no nitrogenous base for one or more residues of the polymer (see Arnold et al., U.S. Pat. No. 5,585,481). A probe may comprise only conventional sugars, bases and linkages found in RNA and DNA, or may include both conventional components and substitutions (e.g., conventional bases linked via a methoxy backbone, or a nucleic acid including conventional bases and one or more base analogs).

While oligonucleotide probes of different lengths and base composition may be used for detecting the nucleic acids of HIV-1, HIV-2, or the combination of HIV-1 and HIV-2, preferred probes in this invention have lengths of up to 100 nucleotides, and more preferably have lengths of up to 60 nucleotides. Preferred length ranges for the invented oligonucleotides are from 10 to 100 bases in length, or more preferably between 15 and 50 bases in length, or still more preferably between 15 and 30 bases in length. However, the specific probe sequences described below also may be provided in a nucleic acid cloning vector or transcript or other longer nucleic acid and still can be used for detecting target nucleic acids. Thus, useful probes in accordance with the invention can include a target-complementary sequence of bases which are of limited length, and one or more appended sequences which are not complementary to the target sequence that is to be detected. For example, a molecular beacon would include a target-complementary loop sequence flanked by "arm" sequences which are not complementary to the target that is to be detected.

Selection of Amplification Primers and Detection Probes

Useful guidelines for designing amplification primers and probes with desired characteristics are described herein. The optimal sites for amplifying and probing HIV-1 and/or HIV-2 nucleic acids contain two, and preferably three, conserved regions each greater than about 10-15 bases in length, within about 200-300 bases of contiguous sequence. The degree of amplification observed with a set of primers or promoter-primers depends on several factors, including the ability of the oligonucleotides to hybridize to their complementary sequences and their ability to be extended enzymatically. Because the extent and specificity of hybridization reactions are affected by a number of factors, manipulation of those factors will determine the exact sensitivity and specificity of a particular oligonucleotide, whether perfectly complementary to its target or not. The effects of varying assay conditions are known to those skilled in the art, and are described by Hogan et al., in U.S. Pat. No. 5,840,488, the disclosure of which is hereby incorporated by reference.

The length of the target nucleic acid sequence and, accordingly, the length of the primer sequence or probe sequence can be important. In some cases, there may be several sequences from a particular target region, varying in location and length, which will yield primers or probes having the desired hybridization characteristics. While it is possible for nucleic acids that are not perfectly complementary to hybridize, the longest stretch of perfectly homologous base sequence will normally primarily determine hybrid stability.

Amplification primers and probes should be positioned to minimize the stability of the oligonucleotide:nontarget (i.e., nucleic acid with similar sequence to target nucleic acid) nucleic acid hybrid. It is preferred that the amplification primers and detection probes are able to distinguish between target and non-target sequences. In designing primers and probes, the differences in these Tm values should be as large as possible (e.g., at least 2° C. and preferably 5° C.).

The degree of non-specific extension (primer-dimer or non-target copying) can also affect amplification efficiency. For this reason, primers are selected to have low self- or cross-complementarity, particularly at the 3' ends of the sequence. Long homopolymer tracts and high GC content are avoided to reduce spurious primer extension. Commercially available computer software can aid in this aspect of the design. Available computer programs include MacDNASIS™ 2.0 (Hitachi Software Engineering American Ltd.) and OLIGO ver. 6.6 (Molecular Biology Insights; Cascade, Colo.).

Those having an ordinary level of skill in the art will appreciate that hybridization involves the association of two single strands of complementary nucleic acid to form a hydrogen bonded double strand. It is implicit that if one of the two strands is wholly or partially involved in a hybrid, then that strand will be less able to participate in formation of a new hybrid. By designing primers and probes so that substantial portions of the sequences of interest are single stranded, the rate and extent of hybridization may be greatly increased. If the target is an integrated genomic sequence, then it will naturally occur in a double stranded form (as is the case with the product of the polymerase chain reaction). These double-stranded targets are naturally inhibitory to hybridization with a probe and require denaturation prior to the hybridization step.

The rate at which a polynucleotide hybridizes to its target is a measure of the thermal stability of the target secondary structure in the target binding region. The standard measurement of hybridization rate is the $C_0t_{1/2}$ which is measured as moles of nucleotide per liter multiplied by seconds. Thus, it is the concentration of probe multiplied by the time at which 50% of maximal hybridization occurs at that concentration. This value is determined by hybridizing various amounts of polynucleotide to a constant amount of target for a fixed time. The $C_0t_{1/2}$ is found graphically by standard procedures familiar to those having an ordinary level of skill in the art.

Preferred Amplification Primers

Primers useful for conducting amplification reactions can have different lengths to accommodate the presence of extraneous sequences that do not participate in target binding, and that may not substantially affect amplification or detection procedures. For example, promoter-primers useful for performing amplification reactions in accordance with the invention have at least a minimal sequence that hybridizes to the target nucleic acid, and a promoter sequence positioned upstream of that minimal sequence. However, insertion of sequences between the target binding sequence and the promoter sequence could change the length of the primer without compromising its utility in the amplification reaction. Additionally, the lengths of the amplification primers and detection probes are matters of choice as long as the sequences of these oligonucleotides conform to the minimal essential requirements for hybridizing the desired complementary sequence.

Tables 1 and 2 present specific examples of oligonucleotide sequences that were used as primers for amplifying HIV-1, HIV-2, or the combination of HIV-1 and HIV-2 nucleic acids in the region encoding p31 integrase. Table 1 presents the sequences of primers that were substantially complementary to one strand of the different nucleic acid targets. The illustrative primers presented in Table 1 have target-complementary sequences that include a 17-mer core sequence of ACARYAGTACWAATGGC (SEQ ID NO:10) (where "R" represents A/G, and "W" represents A or T/U), allowing for the substitution of up to one, or even up to two base analogs. Inosine is an example of a highly preferred base analog that can be used for this purpose, and position 5 and/or position 11 of the core sequence can be substituted with this base analog with very good results. It is preferred for one of the primers used in the amplification procedure to have a target-complementary sequence that contains this 17-mer core. The primer may further include several nucleotides appended to the upstream terminus of the core sequence, and may include a few nucleotides appended to the downstream terminus of the core sequence. For example, there can be five, or even more nucleotides appended to the upstream terminus. It is convenient to include one, two, or three nucleotides appended to the downstream terminus, if desired. Table 2 presents the sequences of the target-complementary primers and the full sequences for promoter-primers that were used during development of the invention. Notably, the oligonucleotide sequences in Table 1 and Table 2 are substantially complementary to opposite strands of the target nucleic acid to be amplified.

Primers useful for amplifying the HIV-1 and/or HIV-2 nucleic acid targets can include nucleotide analogs. For example, when compared with the basic primer sequence of SEQ ID NO:5, primers having SEQ ID NO:6, SEQ ID NO:7 and SEQ ID NO:9 differ by the presence of a single inosine residue at position 16, substitution of a T residue for a C at position 10 and an inosine residue at position 16, or inosine substitutions at positions 10 and 16, respectively. As confirmed by the experimental findings presented herein, these base differences conferred beneficial properties that could not have been predicted in advance of the discovery described herein. More specifically, the results demonstrated that one of these mutant primers, when paired with a single opposite-strand primer, lost specificity for the HIV-1 template and acquired the capacity for amplifying both HIV-1 and HIV-2 templates with substantially equal efficiency. This illustrates how certain positions in the primers may be substituted by modified bases or base analogs.

TABLE 1

Polynucleotide Sequences of Amplification Primers

| Sequence | Identifier |
| --- | --- |
| ACAGCAGTACAAATGGCAG | SEQ ID NO: 1 |
| ACAACAGTACAAATGGCAGT | SEQ ID NO: 2 |
| ACAATAGTACTAATGGCAGT | SEQ ID NO: 3 |
| TTAAGACAGCAGTACAAATGGC | SEQ ID NO: 4 |
| TAGAGACAGCAGTACAAATGGC | SEQ ID NO: 5 |
| TAGAGACAGCAGTACIAATGGC | SEQ ID NO: 6 |

TABLE 1-continued

Polynucleotide Sequences of Amplification Primers

| Sequence | Identifier |
| --- | --- |
| TAGAGACAGTAGTACIAATGGC | SEQ ID NO: 7 |
| TAGAGACAGCAGTACTAATGGC | SEQ ID NO: 8 |
| TAGAGACAGIAGTACIAATGGC | SEQ ID NO: 9 |

Table 2 presents target-complementary oligonucleotide sequences and the corresponding promoter-primer sequences that were used for amplifying HIV-1 and HIV-2 nucleic acid sequences. As indicated above, all promoter-primers included sequences that were substantially complementary to, meaning that they were able to hybridize to, a target sequence at their 3' ends, and a T7 promoter sequence at their 5' ends. Primers identified by SEQ ID NOs: 17-22 in Table 2 are promoter-primers corresponding to the primers identified as SEQ ID NOs: 11-16, respectively. Bases corresponding to T7 promoter sequences in the table are underlined.

TABLE 2

Polynucleotide Sequences of Amplification Primers

| Feature | Sequence | Identifier |
| --- | --- | --- |
| Target-complementary | ATTTCTTGTTCTGTGGTAATCATGTTG | SEQ ID NO: 11 |
| Target-complementary | TTGTTTTTGTAATAGTTGTATTTCTTGTTCTG | SEQ ID NO: 12 |
| Target-complementary | GTTTGTATGTCTGTTGCTATTATGTCTATTAGTCTTTCTGCTGG | SEQ ID NO: 13 |
| Target-complementary | GTTTGTATGTCTGTTGCTATCATGTTGATTATTCTTTC | SEQ ID NO: 14 |
| Target-complementary | ATTTGTTTTTGTAATTCTTGTATTTCTATGTCTGT | SEQ ID NO: 15 |
| Target-complementary | GTTTGTATGTCTGTTGCTATTATGTCTA | SEQ ID NO: 16 |
| T7 Promoter-Primer | <u>AATTTAATACGACTCACTATAGGGAGA</u>ATTTCTTGTTCTGTGGTAATCATGTTG | SEQ ID NO: 17 |
| T7 Promoter-Primer | <u>AATTTAATACGACTCACTATAGGGAGA</u>TTGTTTTTGTAATAGTTGTATTTCTTGTTCTG | SEQ ID NO: 18 |
| T7 Promoter-Primer | <u>AATTTAATACGACTCACTATAGGGAGA</u>GTTTGTATGTCTGTTGCTATTATGTCTATTAGTCTTTCTGCTGG | SEQ ID NO: 19 |
| T7 Promoter-Primer | <u>AATTTAATACGACTCACTATAGGGAGA</u>GTTTGTATGTCTGTTGCTATCATGTTGATTATTCTTTC | SEQ ID NO: 20 |
| T7 Promoter-Primer | <u>AATTTAATACGACTCACTATAGGGAGA</u>ATTTGTTTTTGTAATTCTTGTATTTCTATGTCTGT | SEQ ID NO: 21 |
| T7 Promoter-Primer | <u>AATTTAATACGACTCACTATAGGGAGA</u>GTTTGTATGTCTGTTGCTATTATGTCTA | SEQ ID NO: 22 |

Preferred sets of primers for amplifying HIV-1, HIV-2, or the combination of HIV-1 and HIV-2 sequences in the region encoding the p31 integrase included a first primer that hybridized the target nucleic acid to be amplified (such as one of the primers listed in Table 2) and a second primer that is complementary to the sequence of an extension product of the first primer (such as one of the primer sequences listed in Table 1). In a highly preferred embodiment, the first primer is a promoter-primer that includes a T7 promoter sequence at its 5' end.

Preferred Detection Probes

Another aspect of the invention relates to oligonucleotides that can be used as hybridization probes for detecting HIV-1, HIV-2, or the combination of HIV-1 and HIV-2 nucleic acids. Indeed, methods for amplifying a target sequence present in the nucleic acid of HIV-1 or HIV-2 can include an optional further step for detecting amplicons. This procedure for detecting HIV-1 and/or HIV-2 nucleic acids includes a step for contacting a test sample with a hybridization assay probe that hybridizes to the target nucleic acid sequence, or the complement thereof, under stringent hybridization conditions, thereby forming a probe:target duplex that is stable for detection. Next there is a step for determining whether the hybrid is present in the test sample as an indication of the presence or absence of HIV-1 or HIV-2 nucleic acid target in the test sample. This may involve detecting the probe:target duplex, and preferably involves homogeneous assay systems.

Hybridization assay probes useful for detecting HIV-1, HIV-2, or the combination of HIV-1 and HIV-2 nucleic acids include a sequence of bases substantially complementary to these target nucleic acid sequences. Thus, probes of the invention hybridize one strand of a target nucleic acid sequence, or the complement thereof. These probes optionally may have additional bases outside of the targeted nucleic acid region which may or may not be complementary to the target nucleic acid that is to be detected.

Preferred probes are sufficiently homologous to the target nucleic acid to hybridize under stringent hybridization conditions corresponding to about 60° C. when the salt concentration is in the range of 0.6-0.9 M. Preferred salts include lithium chloride, but other salts such as sodium chloride and sodium citrate also can be used in the hybridization solution. Example high stringency hybridization conditions are alternatively provided by 0.48 M sodium phosphate buffer, 0.1% sodium dodecyl sulfate, and 1 mM each of EDTA and EGTA, or by 0.6 M LiCl, 1% lithium lauryl sulfate, 60 mM lithium succinate and 10 mM each of EDTA and EGTA.

Probes in accordance with the invention have sequences substantially complementary to, or substantially corresponding to portions of the HIV-1 and HIV-2 genomes. Certain probes that are preferred for detecting HIV-1, HIV-2, or the combination of HIV-1 and HIV-2 nucleic acid sequences have a probe sequence which includes a target-complementary sequence of bases, and optionally one or more base sequences that are not complementary to the nucleic acid that is to be detected. The target-complementary sequence of bases preferably is in the length range of from 10-100 nucleotides and is able to hybridize to the amplified nucleic acid. Certain preferred probes that are capable of detecting HIV-1, HIV-2, or the combination of HIV-1 and HIV-2 nucleic acid sequences have target-complementary sequences in the length range of from 10-100, from 15-60, from 15-45 or from 20-30 nucleotides. Of course, these target-complementary sequences may be linear sequences, or may be contained in the structure of a molecular beacon, a molecular torch or other construct having one or more optional nucleic acid sequences that are non-complementary to the target sequence that is to be detected. As indicated above, probes may be made of DNA, RNA, a combination DNA and RNA, a nucleic acid analog, or contain one or more modified nucleosides (e.g., a ribonucleoside having a 2'-O-methyl substitution to the ribofuranosyl moiety).

Certain probes in accordance with the present invention include a detectable label. In one embodiment this label is joined to the probe by means of a non-nucleotide linker. For example, detection probes can be labeled with chemiluminescent acridinium ester compounds that are attached via a linker substantially as described in U.S. Pat. No. 5,585,481; and in U. S. Pat. No. 5,639,604, particularly as described at column 10, line 6 to column 11, line 3, and in Example 8. The disclosures contained in these patent documents are hereby incorporated by reference.

Table 3 presents the base sequences of some of the hybridization probes that were used for detecting HIV-1 target sequences, HIV-2 target sequences, or both HIV-1 and HIV-2 target sequences. Since alternative probes for detecting these target nucleic acids can hybridize to opposite-sense strands, the present invention also includes oligonucleotides that are complementary to the sequences presented in the table.

TABLE 3

Polynucleotide Sequences of Detection Probes

| Sequence | Identifier |
| --- | --- |
| CCTGAATTTTAAAAGAAGGGGG | SEQ ID NO: 23 |
| CCAGAATTTTAAAAGAAGGGGIGG | SEQ ID NO: 24 |
| CCACAATTTTAAAAGAAGGGGIGG | SEQ ID NO: 25 |
| CCTGAATTTTAAAAGAAGGGGIGG | SEQ ID NO: 26 |
| CATGAATTTTAAAAGAAGGGGA | SEQ ID NO: 27 |
| CCTGAATTTTAAAAGAAIGGGG | SEQ ID NO: 28 |
| CCIGAATTTTAAAAGAAGGGGG | SEQ ID NO: 29 |
| CCIIAATTTTAAAAGAAGGGGG | SEQ ID NO: 30 |
| AAAGAAIGGIGGGGATIGGGIGG | SEQ ID NO: 31 |
| AAAGAAIGGIGGGGATTGGGIGG | SEQ ID NO: 32 |
| AATTTTAAAAGAAGAGGIGGGATTGGGGG | SEQ ID NO: 33 |
| CAATTTTAAAAGAAGGGGIGGG | SEQ ID NO: 34 |
| GAATTTTAAAAGAAGIGGGGIG | SEQ ID NO: 35 |
| GAAUUUUAAAAGAAGGGGIGGG | SEQ ID NO: 36 |

As indicated above, any number of different backbone structures can be used as a scaffold for the base sequences of the invented hybridization probes. In certain highly preferred embodiments, the probe includes a methoxy backbone, or at least one methoxy linkage in the nucleic acid backbone.

Selection and Use of Capture Oligonucleotides

Preferred capture oligonucleotides include a first sequence that is substantially complementary to a target sequence (i.e., a "target-complementary" sequence) covalently attached to a second sequence (i.e., a "tail" sequence) that serves as a target for immobilization on a solid support. Any backbone to link the base sequence of a capture oligonucleotide may be used. In certain preferred embodiments the capture oligonucleotide includes at least one methoxy linkage in the backbone. The tail sequence, which is preferably at the 3' end of a capture oligonucieotide, is used to hybridize to a complementary base sequence to provide a means for capturing the hybridized target nucleic acid in preference to other components in the biological sample.

Although any base sequence that hybridizes to a complementary base sequence may be used in the tail sequence, it is preferred that the hybridizing sequence span a length of about 5-50 nucleotide residues. Particularly preferred tail sequences are substantially homopolymeric, containing about 10 to about 40 nucleotide residues, or more preferably about 14 to about 30 residues. A capture oligonucleotide according to the present invention may include a first sequence that hybridizes to a target polynucleotide, and a second sequence that hybridizes to an oligo(dT) stretch immobilized to a solid support.

Using the components illustrated in FIG. 1, one assay for detecting HIV-1, HIV-2, or the combination of HIV-1 and HIV-2 sequences in a biological sample includes the steps of capturing the target nucleic acid using the capture oligonucleotide, amplifying the captured target region using at least two primers, and detecting the amplified nucleic acid by first hybridizing a labeled probe to a sequence contained in the amplified nucleic acid, and then detecting a signal resulting from the bound labeled probe.

The capturing step preferably uses a capture oligonucleotide where, under hybridizing conditions, one portion of the capture oligonucleotide specifically hybridizes to a sequence in the target nucleic acid and a tail portion serves as one component of a binding pair, such as a ligand (e.g., a biotin-avidin binding pair) that allows the target region to be separated from other components of the sample. Preferably, the tail portion of the capture oligonucleotide is a sequence that hybridizes to a complementary sequence immobilized to a solid support particle. Preferably, first, the capture oligonucleotide and the target nucleic acid are in solution to take advantage of solution phase hybridization kinetics. Hybridization produces a capture oligonucleotide:target nucleic acid complex which can bind an immobilized probe through hybridization of the tail portion of the capture oligonucleotide with a complementary immobilized sequence. Thus, a complex comprising a target nucleic acid, capture oligonucleotide and immobilized probe is formed under hybridization conditions. Preferably, the immobilized probe is a repetitious sequence, and more preferably a homopolymeric sequence (e.g., poly-A, poly-T, poly-C or poly-G), which is complementary to the tail sequence and attached to a solid support. For example, if the tail portion of the capture oligonucleotide contains a poly-A sequence, then the immobilized probe would contain a poly-T sequence, although any combination of complementary sequences may be used. The capture oligonucleotide may also contain "spacer" residues, which are one or more bases located between the base sequence that hybridizes to the target and the base sequence of the tail that hybridizes to the immobilized probe. Any solid support may be used for binding the target nucleic acid:capture oligonucleotide complex. Useful supports may be either matrices or particles free in solution (e.g., nitrocellulose, nylon, glass, polyacrylate, mixed polymers, polystyrene, silane polypropylene and, preferably, magnetically attractable particles). Methods of attaching an immobilized probe to the solid support are well known. The support is preferably a particle which can be retrieved from solution using standard methods (e.g., centrifugation, magnetic attraction of magnetic particles, and the like). Preferred supports are paramagnetic monodisperse particles (i.e., uniform in size±about 5%).

Retrieving the target nucleic acid:capture oligonucleotide:immobilized probe complex effectively concentrates the target nucleic acid (relative to its concentration in the biological sample) and purifies the target nucleic acid from amplification inhibitors which may be present in the biological sample. The captured target nucleic acid may be washed one or more times, further purifying the target, for example, by resuspending the particles with the attached target nucleic acid:capture oligonucleotide:immobilized probe complex in a washing solution and then retrieving the particles with the attached complex from the washing solution as described above. In a preferred embodiment, the capturing step takes place by sequentially hybridizing the capture oligonucleotide with the target nucleic acid and then adjusting the hybridization conditions to allow hybridization of the tail portion of the capture oligonucleotide with an immobilized complementary sequence (e.g., as described in PCT No. WO 98/50583). After the capturing step and any optional washing steps have been completed, the target nucleic acid can then be amplified. To limit the number of handling steps, the target nucleic acid optionally can be amplified without releasing it from the capture oligonucleotide.

Useful capture oligonucleotides may also contain mismatches to the sequence of the nucleic acid molecule that is to be amplified. Successful target capture and nucleic acid amplification can be achieved as long as the mismatched sequences hybridize to the nucleic acid molecule containing the sequence that is to be amplified. Indeed, oligonucleotides for the capture of HIV-1 nucleic acids, as described in the published international patent application identified by WO 03/106714, were used to practice the methods disclosed herein, including methods of detecting HIV-2.

Preferred Methods for Amplifying and Detecting Target Polynucleotide Sequences

Preferred methods of the present invention are described and illustrated by the Examples presented below. FIG. 1 schematically illustrates one system that may be used for detecting a target region of the viral genome (shown by a thick solid horizontal line). This basic system includes four oligonucleotides (shown by the shorter solid lines): one capture oligonucleotide that includes a sequence that hybridizes to a sequence in the target region and a tail ("T") that hybridizes to a complementary sequence immobilized on a solid support to capture the target region present in a biological sample; one T7 promoter-primer which includes a sequence that hybridizes specifically to an HIV-1 or HIV-2 sequence in the target region and a T7 promoter sequence ("P") which, when double-stranded, serves as a functional promoter for T7 RNA polymerase; one non-T7 primer which includes a sequence that hybridizes specifically to a first strand cDNA made from the target region sequence using the T7 promoter-primer; and one labeled probe which includes a sequence that hybridizes specifically to a portion of the target region that is amplified using the two primers.

As indicated above, amplifying the captured target region using the two primers can be accomplished by any of a variety of known nucleic acid amplification reactions that will be familiar to those having an ordinary level of skill in the art. In a preferred embodiment, a transcription-associated amplification reaction, such as TMA, is employed. In such an embodiment, many strands of nucleic acid are produced from a single copy of target nucleic acid, thus permitting detection of the target by detecting probes that are bound to the amplified sequences. Preferably, transcription-associated amplification uses two types of primers (one being referred to as a promoter-primer because it contains a promoter sequence, labeled "P" in FIG. 1, for an RNA polymerase) two enzymes (a reverse transcriptase and an RNA polymerase), and substrates (deoxyribonucleoside triphosphates, ribonucleoside triphosphates) with appropriate salts and buffers in solution to produce multiple RNA transcripts from a nucleic acid template.

Referring to FIG. 1, during transcription-mediated amplification, the captured target nucleic acid is hybridized to a first primer (shown as a T7 promoter-primer). Using reverse transcriptase, a complementary DNA strand is synthesized from the T7 promoter-primer using the target RNA as a template. A second primer, shown as a non-T7 primer, hybridizes to the newly synthesized DNA strand and is extended by the action of a reverse transcriptase to form a DNA duplex, thereby forming a double-stranded T7 promoter region. T7 RNA polymerase then generates multiple RNA transcripts by using this functional T7 promoter. The autocatalytic mechanism of TMA employs repetitive hybridization and polymerization steps following a cDNA synthesis step using the RNA transcripts as templates to produce additional transcripts, thereby amplifying target region-specific nucleic acid sequences.

The detecting step uses at least one detection probe that binds specifically to the amplified RNA transcripts or amplicons described above. Preferably, the detection probe is labeled with a label that can be detected using a homogeneous detection system. For example, the labeled probe can be labeled with an acridinium ester compound from which a chemiluminescent signal may be produced and detected, as described above. Alternatively, the labeled probe may comprise a fluorophore or a paired fluorophore and quencher moiety set. A molecular beacon is one embodiment of such a labeled probe that may be used in a homogeneous detection system.

Methods of Detecting HIV-1 and/or HIV-2 Nucleic Acids

Three distinct methods of detecting HIV-1 and HIV-2 nucleic acids in multiplex assays also have been invented. Each method is distinguished from the other by the use of primers that are cross-reactive or analyte-specific, and also by the use of probes that are cross-reactive or analyte-specific.

In the first invented method, independent sets of analyte-specific primers, meaning a first set of primers specific for HIV-1 nucleic acids (but not HIV-2 nucleic acids) and a second set of primers specific for HIV-2 nucleic acids (but not HIV-1 nucleic acids), are used for synthesizing amplicons in a single amplification reaction. The synthesized amplicons are subsequently detected using a cross-reactive probe which is able to detect both HIV-1 amplicons and HIV-2 amplicons. Positive hybridization results obtained using this method indicate that the test sample which provided nucleic acid templates for amplification contains either HIV-1 or HIV-2, without distinguishing between the two analytes.

In the second invented method, a set of cross-reactive primers is used for synthesizing HIV-1 amplicons and/or HIV-2 amplicons in a single amplification reaction. The synthesized amplicons are subsequently detected using distinct, analyte-specific probes. One of the probes is specific for HIV-1 amplicons (but not HIV-2 amplicons) while another of the probes is specific for HIV-2 amplicons (but not HIV-1 amplicons). The step for detecting amplicons synthesized using the cross-reactive primers can involve either combining the analyte-specific probes in a single hybridization reaction, or separately hybridizing each of the analyte-specific probes with aliquots containing the products of the amplification reaction. If the probes are combined in a single hybridization reaction, then a positive result indicates that a test sample contains either HIV-1 or HIV-2, without distinguishing between the two analytes. Alternatively, if the probes are separately hybridized with independent aliquots of the amplification reaction, then a positive result in one of the hybridization reactions will indicate that the analyte complementary to the probe contained in the reaction was present in the test sample that provided nucleic acid templates for amplification.

In the third invented method, a set of cross-reactive primers is used for synthesizing HIV-1 amplicons and/or HIV-2 amplicons in a single amplification reaction. The synthesized amplicons are subsequently detected using a cross-reactive probe which is able to detect both HIV-1 amplicons and HIV-2 amplicons. Positive hybridization results obtained using this method indicate that the test sample which provided nucleic acid templates for amplification contains either HIV-1 or HIV-2, without distinguishing between the two analytes.

The invented cross-reactive primers are particularly useful in multiplex reactions for amplifying HIV-1 and/or HIV-2. Conventional multiplex reactions typically involve the use of a few, or even several independent primer sets, with each set of primers being capable of amplifying a different analyte nucleic acid that may be present in a sample undergoing testing. When the number of primers reaches a threshold value, there is the possibility for undesirable primer-primer interactions to occur. When this is the case, the primers can be consumed in the production of undesirable extension products, thereby inhibiting the efficient synthesis of analyte-specific amplicons. A solution to this problem is to use cross-reactive primers that allow amplification of multiple analytes, thereby reducing the number of primer species that must be included in the reaction.

Another benefit of the invented cross-reactive primers and probes also relates to multiplex amplification reactions. More particularly, the preferred use of at least one cross-reactive primer, and more preferably at least one set of two cross-reactive primers, in a multiplex amplification reaction affords redundancy in the detection of at least one of the subject analytes. This redundant detection is highly advantageous when one of the analytes is prone to mutation or exists in alternative forms that could be missed by the use of a single set of amplification primers. For example, if a multiplex amplification reaction is a capable of detecting HIV-1 and HIV-2, it is desirable, in accordance with the present invention, to carry out amplification reactions using at least one set of primers that are capable of amplifying both HIV-1 and HIV-2. When this is the case, the cross-reactive primers will provide a redundant means for amplifying the HIV-1 analyte polynucleotide. Similarly, a cross-reacting probe capable of hybridizing HIV-1 amplicons and HIV-2 amplicons provides a redundant means for detecting HIV-1 analyte polynucleotides in a hybridization reaction that contains a probe specific for HIV-1 and not HIV-2.

Notably, the desired level of cross-reactivity among the primers of multiplex assays capable of amplifying portions of more than two analyte polynucleotides is limited. For example, when a multiplex reaction is capable of amplifying portions of three different analyte polynucleotides, a set of cross-reacting primers in accordance with the invention should be capable of amplifying portions of only two of the three analytes. When a multiplex reaction is capable of amplifying portions of four different analyte polynucleotides, a set of cross-reacting primers in accordance with the invention should be capable of amplifying portions of either only two of the four analytes or only three of the four analytes. Generally speaking, a set of cross-reacting primers in accordance with the invention should be capable of amplifying portions of fewer than the total number of analyte polynucleotides that can be amplified in the multiplex reaction. This clearly is distinct from a situation in which all polynucleotide analytes of a multiplex reaction are amplified, as may be the case when one of the primers in a reaction is an oligo dT primer.

Kits for Detecting HIV-1 HIV-2, or the Combination of HIV-1 and HIV-2 Nucleic Acids The present invention also embraces kits for performing polynucleotide amplification reactions using viral nucleic acid templates. Certain preferred kits include a hybridization assay probe that has a target-complementary sequence of bases, and optionally include primers or other ancilary oligonucleotides for amplifying the target that is to be detected by the hybridization assay probe. Other preferred kits contain a pair of oligonucleotide primers that may be used for amplifying target nucleic acids in an in vitro amplification reaction. Exemplary kits include first and second amplification oligonucleotides or primers that are complementary to opposite strands of a target nucleic acid sequence that is to be amplified. The kits may further contain one or more probes for detecting the amplification products synthesized by the action of the primers which are contained in the kit. Still other kits in accordance with the invention may additionally include capture oligonucleotides for purifying template nucleic acids away from other species prior to amplification.

The general principles of the present invention may be more fully appreciated by reference to the following non-limiting Examples.

Example 1 describes procedures that identified some of the hybridization probes which subsequently were used in assays for detecting HIV-1, HIV-2, or the combination of HIV-1 and HIV-2 nucleic acids. More particularly, the following procedures employed synthetic oligonucleotides as targets for hybridization probes. As indicated below, one of the probes tested in the procedure exhibited substantially equivalent specificity for HIV-1 and HIV-2 targets.

EXAMPLE 1

Oligonucleotide Probes for Detecting HIV-1 and/or HIV-2

Synthetic target oligonucleotides were prepared according to standard laboratory procedures using 2'-OMe nucleotide analogs to mimic RNA structures. The model HIV-1 target had the sequence of TCCCCCCTTTTCTTTTAAAAT-TGTGGATGA (SEQ ID NO:37), while the model HIV-2 target had the sequence of TTCCTCCCCTTCTTTTAAAAT-TCATGCAAT (SEQ ID NO:38). Probes for hybridizing these synthetic targets had the sequences given in Table 3, and were also prepared using 2'-OMe nucleotide analogs.

Hybridization reactions included about $2 \times 10^6$ RLUs of AE-labeled probe having a specific activity of about $1-7 \times 10^8$ RLU/pmole, and about 0.5 pmoles of synthetic target oligonucleotide. Negative control reactions omitted the target oligonucleotide. The probes listed in Table 3 were each labeled with an AE moiety joined to the oligonucleotide structure by an internally disposed non-nucleotide linker according to procedures described in U.S. Pat. Nos. 5,585,481 and 5,639,604, the disclosures of these patents having been incorporated by reference hereinabove. The linkers on the probes of SEQ ID NO:23, SEQ ID NO:30, SEQ ID NO:27, SEQ ID NO:28 and SEQ ID NO:29 were located between positions 7 and 8. The linkers on the probes of SEQ ID NO:24 and SEQ ID NO:25 were located between positions 13 and 14. The linker on the probe of SEQ ID NO:26 was located between positions 12 and 13. The linkers on the probes of SEQ ID NO:31 and SEQ ID NO:32 were located between positions 17 and 18. The linker on the probe of SEQ ID NO:33 was located between positions 26 and 27. The linker on the probe of SEQ ID NO:34 was located between positions 9 and 10. The linker on the probe of SEQ ID NO:35 was located between positions 8 and 9. The linker on the probe of SEQ ID NO:36 was located between positions 11 and 12. Use of all of these different linker positions confirmed the versatility of this labeling technique. Probe hybridizations were carried out at 60° C. for 15 minutes in 50 µl volumes of a Tris-buffered solution that included the reagents used in the amplification reaction described in Example 2. Hybridization reactions were followed by addition of an aliquot of 0.15 M sodium tetraborate (pH 8.5), and 1% TRITON X-100 (Union Carbide Corporation; Danbury, Conn.). These mixtures were first incubated at 60° C. for 10 minutes to inactivate the chemiluminescent label joined to unhybridized probe, and cooled briefly to 4° C. prior to reading the hybridization signal. Chemiluminescence due to hybridized probe in each sample was assayed using a LUMISTAR GALAXY luminescence microplate reader (BMG Labtechnologies Inc.; Durham, N.C.) configured for automatic injection of 1 mM nitric acid and 0.1% (v/v) hydrogen peroxide, followed by injection of a solution containing 1 N sodium hydroxide. Results for the chemiluminescent reactions were measured in relative light units (RLU). Representative results from this procedure are summarized in Table 4 for each of the three different target regions. In this procedure, the signal/noise value corresponded to the chemiluminescent signal (measured in RLU) generated by label associated with specifically hybridized probe divided by a background signal measured in the absence of a target nucleic acid. Each value represents the average of 5 replicates.

TABLE 4

Probe Hybridization Results

| p31 Integrase Region Probe | HIV-1 Target (SEQ ID NO: 37) | | HIV-2 Target (SEQ ID NO: 38) | |
|---|---|---|---|---|
| | RLU remaining as % of $T_0$ value | Signal/ Noise | RLU remaining as % of $T_0$ value | Signal/ Noise |
| SEQ ID NO: 23 | 2 | 1 | 101 | 58 |
| SEQ ID NO: 24 | 7 | 1 | 61 | 8 |
| SEQ ID NO: 25 | 110 | 12 | 107 | 11 |
| SEQ ID NO: 26 | 6 | 1 | 72 | 13 |
| SEQ ID NO: 27 | 7 | 1 | 70 | 11 |
| SEQ ID NO: 28 | 1 | 1 | 49 | 35 |
| SEQ ID NO: 29 | 3 | 1 | 57 | 18 |
| SEQ ID NO: 30 | 4 | 1 | 30 | 10 |
| SEQ ID NO: 31 | 80 | 7 | 42 | 4 |
| SEQ ID NO: 32 | 60 | 10 | 14 | 2 |
| SEQ ID NO: 33 | 50 | 34 | 2 | 1 |
| SEQ ID NO: 34 | 21 | 3 | 50 | 8 |
| SEQ ID NO: 35 | 2 | 1 | 54 | 31 |
| SEQ ID NO: 36 | 13 | 1 | 61 | 5 |

The results presented in Table 4 showed that some of the probes tested in the procedure gave a strong hybridization signal following interaction with the one or both of the target sequences. Only some of the probes used in the procedure gave S/N values substantially greater than 10 when hybridized with at least one of the synthetic targets.

Interestingly, very subtle differences distinguished useful probe sequences from each other. For example, when compared with the probe having the sequence of SEQ ID NO:24, the probe of SEQ ID NO:26 differed by only two out of twenty-four nucleotide positions and retained a strong specificity for the HIV-2 target. On the other hand, a probe having the sequence of SEQ ID NO:25 differed from the probe of SEQ ID NO:24 by only one of these two different nucleotide positions and did not exhibit specificity for the HIV-2 target. Indeed, the probe of SEQ ID NO:25 failed to exhibit substantial specificity for either of the two targets and was found to be capable of hybridizing with substantially equal specificity to the HIV-1 and HIV-2 targets. In all three cases, the probes included a single inosine base analog and so did not correspond to any naturally occurring HIV-1 or HIV-2 nucleic acid sequence.

The unusual hybridization properties of the probe having the sequence of SEQ ID NO:25 rendered it highly useful for detecting either HIV-1 or HIV-2. A positive result indicating hybridization of this probe to the products of a multiplex reaction that is capable of amplifying either HIV-1 or HIV-2 indicates that the test sample which provided the nucleic acid templates for amplification contained at least one of the two analytes. Use of the cross-reactive probe of SEQ ID NO:25 as a component in a hybridization probe reagent containing a separate probe specific for HIV-1 (but not HIV-2) advantageously provides a means for redundantly detecting the HIV-1 analyte while simultaneously providing a means for detecting an HIV-2 analyte. Although somewhat less preferred because of reduced signal recovery (see Table 4), a probe having the sequence of SEQ ID NO:31 can be used in place of the probe of SEQ ID NO:25 in applications where it is desirable to employ a probe that is able to hybridize with HIV-1 and HIV-2 nucleic acids.

Highly preferred embodiments of the invention employ the cross-reactive probe of SEQ ID NO:25 for detection of either HIV-1 or HIV-2 nucleic acids. For example, kits can include in packaged combination: the probe of SEQ ID NO:25 and a set of oligonucleotide primers that are specific for HIV-1 (but not HIV-2) and a set of oligonucleotide primers that are specific for HIV-2 (but not HIV-1). An alternative kit can include in packaged combination: the probe of SEQ ID NO:25 and a set of oligonucleotide primers that are cross-reactive with HIV-1 and HIV-2, meaning that they are capable of amplifying both HIV-1 and HIV-2 nucleic acids.

Probes that were useful for detecting HIV-2 nucleic acids, but not HIV-1 nucleic acids, included: SEQ ID NO:23, SEQ ID NO:24, SEQ ID NO:26, SEQ ID NO:27, SEQ ID NO:28, SEQ ID NO:29, SEQ ID NO:30, SEQ ID NO:35, and SEQ ID NO:36.

Preferred primer combinations for amplifying HIV-1, HIV-2, or the combination of HIV-1 and HIV-2 nucleic acids were identified in a series of procedures that employed virions as the source of nucleic acid templates. Promoter-primers and opposite strand primers were screened in combination using the method described below. Although these procedures were particularly carried out using a Transcription Mediated Amplification (TMA) protocol, the primers disclosed herein may be used to produce amplicons by alternative in vitro nucleic acid amplification methods that will be familiar to those having an ordinary level of skill in the art.

Example 2 describes methods that identified primers useful for amplifying the p31 integrase region of HIV-1 and/or HIV-2.

EXAMPLE 2

Identification of Amplification Primers

A high-titer cell lysate containing HIV-2 B6 virus particles served as the source of HIV-2 template sequences in amplification reactions that employed paired sets of primers. Virus-negative serum was used to prepare diluted stocks containing either 100 copies/ml of the HIV-1 nucleic acid template, or 300 copies/ml of the HIV-2 nucleic acid template. In a single instance, a stock containing 100 copies/ml of the HIV-2 nucleic acid template was prepared. Nucleic acids underwent specimen processing and target capture prior to amplification essentially according to the procedures disclosed in published International Patent Application No. PCT/US2000/18685, except that templates were captured using oligonucleotides described in the published international patent application identified by WO 03/106714 for the capture of HIV-1 nucleic acids. Notably, capture oligonucleotides do not participate in the amplification or detection steps of the assay. Virus-containing samples having volumes of 0.5 ml were combined with a target-capture reagent to facilitate nucleic acid release and hybridization to capture oligonucleotides disposed on magnetic beads. TMA reactions were carried out essentially as described by Kacian et al., in U.S. Pat. No. 5,399,491, the disclosure of this U.S. patent having been incorporated by reference hereinabove. Promoter-primers included a T7 promoter sequence AATTTAATACGACTCACTATAGGGAGA (SEQ ID NO:39) upstream of a target-complementary sequence. Amplification reactions were conducted for various primer combinations using 15 pmoles of each primer in 100 µl of reaction buffer. Isolated target nucleic acids were combined with primers in a standard nucleic acid amplification buffer, heated to 60° C. for 10 minutes and then cooled to 42° C. to facilitate primer annealing. Moloney Murine Leukemia Virus (MMLV) reverse transcriptase (5,600 units/reaction) and T7 RNA polymerase (3,500 units/reaction) were then added to the mixtures. Amplification reactions were carried out in a Tris-buffered solution (pH 8.2 to 8.5) containing KCl, deoxyribonucleoside 5'-triphosphates, ribonucleoside 5'-triphosphates, N-Acetyl-L-Cysteine, and 5% (w/v) glycerol, as will be familiar to those having an ordinary level of skill in the art. After a one hour incubation at 42° C., the entire 100 µl amplification reaction was subjected to a hybridization assay essentially as described in Example 1 using an independent HIV-1 specific probe which did not cross-hybridize with HIV-2, and the HIV-2 specific probe of SEQ ID NO:23 which did not cross-hybridize with HIV-1. The probes were labeled with acridinium ester to specific activities of about $1-7\times10^8$ RLU/pmol and then used in amounts equivalent to about $2\times10^6$ RLU for each hybridization reaction. Specifically hybridized probe was quantified following chemical inactivation of the chemiluminescent label associated with non-hybridized probe in a homogeneous assay essentially as described in Example 1. Trials were conducted using replicates of 10. To be judged as a positive result, the chemiluminescent signal indicating probe hybridization must have exceeded 50,000 RLU in an assay.

Table 5 presents results from amplification procedures that were conducted using different combinations of amplification primers. Numerical values appearing in the table represent the percentage of positive trials.

TABLE 5

Amplification of HIV-1 and HIV-2 Polynucleotide Sequences Using Various Primer Combinations

| non-T7 primer | Target (c/ml) | T7 Primer Target-Complementary Sequence | | | | | |
|---|---|---|---|---|---|---|---|
| | | SEQ ID NO: 11 | SEQ ID NO: 12 | SQ ID NO: 13 | SEQ ID NO: 14 | SEQ ID NO: 15 | SEQ ID NO: 16 |
| SEQ ID NO: 1 | HIV1 (100) | 0% | 0% | 100% | ND | ND | 100% |
| | HIV2 (100) | 100% | 100% | 0% | ND | ND | 0% |
| SEQ ID NO: 2 | HIV1 (100) | 0% | 0% | 100% | 100% | 100% | 100% |
| | HIV2 (100) | 100% | 100% | 100% | 100% | 100% | ND |
| | HIV2 (300) | ND | ND | ND | ND | ND | 100% |
| SEQ ID NO: 3 | HIV1 (100) | 0% | ND | ND | ND | ND | ND |
| | HIV2 (100) | 100% | 100% | 100% | ND | ND | ND |
| SEQ ID NO: 4 | HIV1 (100) | ND | ND | ND | 100% | ND | ND |
| | HIV2 (300) | ND | ND | ND | 0% | ND | ND |
| SEQ ID NO: 5 | HIV1 (100) | ND | ND | ND | 100% | ND | ND |
| | HIV2 (300) | ND | ND | ND | 0% | ND | ND |
| SEQ ID NO: 6 | HIV1 (100) | ND | ND | ND | 100% | ND | ND |
| | HIV2 (300) | ND | ND | ND | 0% | ND | ND |
| SEQ ID NO: 7 | HIV1 (100) | ND | ND | ND | 100% | ND | ND |
| | HIV2 (300) | ND | ND | ND | 100% | ND | ND |
| SEQ ID NO: 8 | HIV1 (100) | ND | ND | ND | 100% | ND | ND |
| | HIV2 (300) | ND | ND | ND | 57% | ND | ND |
| SEQ ID NO: 9 | HIV1 (100) | ND | ND | ND | 80% | ND | ND |
| | HIV2 (300) | ND | ND | ND | 50% | ND | ND |

"ND" indicates "not done" (primer pair not tested)

The results presented in Table 5 showed that some of the primer combinations gave very high levels of HIV-1 and HIV-2 detectability, even at levels as low as 50 copies of the viral template per reaction. More specifically, excellent results were obtained using a primer having the target-complementary sequence of SEQ ID NO:2 in combination with a primer having the target-complementary sequence of any of SEQ ID NO:13, SEQ ID NO:14, SEQ ID NO:15, or SEQ ID NO:16. Excellent results also were achieved using a primer having the target-complementary sequence of SEQ ID NO:14 in combination with a primer having the target-complementary sequence of any of SEQ ID NO:7, SEQ ID NO:8, or SEQ ID NO:9. The target-complementary portions of these latter three primers all conformed to the consensus sequence TAGAGACAGNAGTACNAATGGC (SEQ ID NO:40), where position 10 is occupied by C, T or I, and where position 16 is occupied by T or I. Primers conforming to this consensus are preferred for amplifying HIV-1 or HIV-2 target nucleic acids. A combination of primers having the target-complementary sequences of SEQ ID NO:14 and SEQ ID NO:7 advantageously is capable of amplifying the largest number of genetic variants of HIV-1 and HIV-2. Notably, no false-positive reactions were observed in these procedures.

Although the foregoing Example describes assays conducted using independent probes that were specific for HIV-1 (but not for HIV-2) and HIV-2 (but not for HIV-1), the invention also embraces compositions, kits and methods employing probes that are cross-reactive for HIV-1 and HIV-2. Particular examples of cross-reactive probes that can be used in conjunction with any of the above-described primer combinations have the sequences of SEQ ID NO:25 and SEQ ID NO:31.

The ability of a selected set of oligonucleotides to amplify and detect a variety of different HIV-2 isolates was next demonstrated.

Example 3 describes procedures that demonstrated the invented primers and probe were useful for detecting a broad range of HIV-2 isolates.

EXAMPLE 3

Broad Range of Detectability for HIV-2

Primers having the target-complementary sequences of SEQ ID NO:7 and SEQ ID NO. 14 were used in combination for amplifying HIV-2 template nucleic acids from seven different HIV-2 strains that were available as high-titer lysates. These specimens were diluted in virus-negative serum to produce stocks having viral template concentrations of 300 copies/ml. As in the previous Example, virus-containing samples having volumes of 0.5 ml were combined with a target-capture reagent to facilitate nucleic acid release and hybridization to capture oligonucleotides that were disposed on magnetic beads. Amplification reactions were carried out as described in the proceeding Example. Amplicons were detected essentially as described in Example 1, except that an AE-labeled, HIV-2 specific probe having the sequence of SEQ ID NO:23 was used, and the detection step was carried out using a LEADER HC+luminometer (Gen-Probe Incorporated, CA). Assays yielding specific hybridization signals of at least 50,000 RLUs were judged as being positive. All assays were carried out in replicates of ten. Results from these procedures are presented in Table 6.

TABLE 6

Amplification and Detection of Different HIV-2 Isolates

| HIV-2 Strain | % Positive (N = 10) |
|---|---|
| HIV-2 B2 | 100 |
| HIV-2 B3 | 100 |
| HIV-2 B4 | 100 |
| HIV-2 B5 | 100 |
| HIV-2 B7 | 100 |
| HIV-2 B8 | 100 |
| HIV-2 B9 | 100 |

The results presented in Table 6 showed that the cross-reactive primers having the target-complementary sequences of SEQ ID NO:7 and SEQ ID NO:14 were capable of amplifying nucleic acids from a variety of different strains of HIV-2, and similarly that an HIV-2 specific probe having the sequence of SEQ ID NO:23 was capable of detecting nucleic acids from a variety of different HIV-2 strains. These primers and this probe represent preferred embodiments of the invention.

Although the foregoing Example illustrated an assay based on the combined use of cross-reactive primers and an analyte-specific probe, the present invetion also embraces embodiments wherein cross-reactive primers are used in combination, or packaged in a kit, with a probe that also is cross-reactive, meaning that the probe is capable of independently hybridizing to HIV-1 and HIV-2 nucleic acids or amplicons. Particular examples of cross-reactive primers and cross-reactive probes are disclosed herein. For instance, the illustrative HIV-2 specific probe used in this Example could have been substituted by one of the cross-reactive probes identified by SEQ ID NO:25 or SEQ ID NO:31.

The following Example demonstrates that two different primer combinations were capable of amplifying an HIV-2 template nucleic acid at an amount equal to 150 copies/reaction. Significantly, these amplification and detection procedures were performed in a reaction mixture that was capable of multiplex amplification of HIV-1, HIV-2, HBV and HCV. These results showed that the presence of primers specific for extraneous targets did not adversely impact detection of HIV-2.

Example 4 describes procedures that demonstrated how the invented primers could be combined in a multiplex nucleic acid amplification reaction capable of detecting HIV-1, HIV-2, HBV and HCV.

EXAMPLE 4

Amplification of HIV-2 Nucleic Acids in a Multiplex Assay

Primers having the sequences of SEQ ID NO:20 (target-complementary sequence of SEQ ID NO:14) and either SEQ ID NO:2 or SEQ ID NO:7 were added to a reaction formulation that included primers capable of amplifying analytes that included HIV-1, HBV and HCV. Multiplex assay formulations for performing target capture, amplification and probe-based detection of these targets are disclosed in the published international patent application identified by WO 03/106714, the disclosure of which is incorporated by reference. As in Example 2, samples containing HIV-1 virions or HIV-2 virions were prepared by diluting high-titer stocks with virus-negative serum. Target capture and nucleic acid amplification reactions were performed using 0.5 ml of diluted virus sample, as described herein. Detection of HIV-2 amplicons by the procedures described above was carried out using the HIV-2 specific probe of SEQ ID NO:23, together with probes specific for detecting HIV-1, HBV and HCV amplicons. Assays yielding specific hybridization signals of at least 50,000 RLUs were judged as being positive. Results from these procedures appear in Table 7.

TABLE 7

Detection of HIV-2 in a Multiplex Assay

| Target-Complementary Primer Sequences | Target | % Positive |
|---|---|---|
| SEQ ID NO: 2 | HIV-1 Type B (100 c/ml) | 100% (N = 10) |
| SEQ ID NO: 14 | HIV-2 B8 (300 c/ml) | 100% (N = 10) |
| SEQ ID NO: 7 | HIV-1 Type B (100 c/ml) | 100% (N = 40) |
| SEQ ID NO: 14 | HIV-2 B7 (300 c/ml) | 100% (N = 40) |

The results presented in Table 7 confirmed that different combinations of the invented primers were capable of efficiently detecting HIV-2 target nucleic acids in multiplex reactions that were also capable of amplifying and detecting HIV-1, HBV and HCV.

In addition to the above-described assay which detects HIV-1 and HIV-2 sequences in the regions encoding the p31 integrase, a second target region, located within the gene encoding the p51 reverse transcriptase (RT), was also found to be useful for detecting HIV-1 and HIV-2 nucleic acids. Methods used to make this second demonstration were essentially as described above. Oligonucleotide probes used in the procedures for identifying cross-reactive probes in the p51 RT target region had the sequences presented in the Table 8.

TABLE 8

| Sequences of Detection Probes | |
|---|---|
| Sequence | Identifier |
| AGGCAGUAUACUGCAUUUACCIUACC | SEQ ID NO: 41 |
| GTATACTGCATTTACCCTACC | SEQ ID NO: 42 |
| AGGAAGUAUACUGCAUUUACCIUACC | SEQ ID NO: 43 |
| AGGAAGUAUACUGCAUUUACCAUACC | SEQ ID NO: 44 |

Example 5 describes procedures used to identify candidate cross-reactive probes that hybridized to the p51 RT regions of HIV-1 and HIV-2 nucleic acids.

EXAMPLE 5

Oligonucleotide Probes for Detecting HIV-1 and/or HIV-2

Synthetic target oligonucleotides were prepared according to standard laboratory procedures. The model HIV-1 target had the sequence of CUAGGUAUGGUAAAUG-CAGUAUACUUC (SEQ ID NO:45), while the model HIV-2 target had the sequence of GAUGGUAGGGUAAAUG-CAGUAUACU (SEQ ID NO:46). The HIV-1 and HIV-2 targets were both synthesized using RNA precursors. Probes for hybridizing these synthetic targets had the sequences given in Table 8, and were prepared using 2'-OMe nucleotide analogs.

Hybridization reactions included about $2 \times 10^6$ RLUs of AE-labeled probe having a specific activity of about $1-7 \times 10^8$ RLU/pmole, and about 0.5 pmoles of synthetic target oligonucleotide. Negative control reactions omitted the target oligonucleotide. The probes listed in Table 8 were each labeled with an AE moiety joined to the oligonucleotide structure by an internally disposed non-nucleotide linker according to procedures described in U.S. Pat. Nos. 5,585,481 and 5,639,604, the disclosures of these patents having been incorporated by reference hereinabove. The linker on the probe of SEQ ID NO:42 alternatively was located between nucleotides 7 and 8, between nucleotides 11 and 12, or between nucleotides 12 and 13. The linkers on the probes of SEQ ID NO:41, SEQ ID NO:43, and SEQ ID NO:44 were all located between nucleotides 12 and 13. Use of these different linker positions confirmed the versatility of this labeling technique. Probe hybridizations were carried out at 60° C. for 15 minutes in 50 µl volumes of a Tris-buffered solution that included the reagents used in the amplification reaction described in Example 2. Hybridization reactions were followed by addition of an aliquot of 0.15 M sodium tetraborate (pH 8.5), and 1% TRITON X-100 (Union Carbide Corporation; Danbury, Conn.). These mixtures were first incubated at 60° C. for 10 minutes to inactivate the chemiluminescent label joined to unhybridized probe, and cooled briefly to 4° C. prior to reading the hybridization signal. Chemiluminescence due to hybridized probe in each sample was assayed using a LUMISTAR GALAXY luminescence microplate reader (BMG Labtechnologies Inc.; Durham, N.C.) configured for automatic injection of 1 mM nitric acid and 0.1% (v/v) hydrogen peroxide, followed by injection of a solution containing 1 N sodium hydroxide. Results for the chemiluminescent reactions were measured in relative light units (RLU). Representative results from this procedure are summarized in Table 9 for each of the three different probe sequences. In this procedure, the signal/noise value corresponded to the chemiluminescent signal (measured in RLU) generated by label associated with specifically hybridized probe divided by a background signal measured in the absence of a target nucleic acid. Each value represents the average of 5 replicates.

TABLE 9

Probe Hybridization Results

| p51 RT Region Probe | HIV-1 Target (SEQ ID NO: 45) | | HIV-2 Target (SEQ ID NO: 46) | |
|---|---|---|---|---|
| | RLU remaining as % of $T_0$ value | Signal/ Noise | RLU remaining as % of $T_0$ value | Signal/ Noise |
| SEQ ID NO: 41 | 66.7 | 5.1 | 66.1 | 5.0 |
| SEQ ID NO: 42 | 111.4 | 296.2 | 101.5 | 269.8 |
| SEQ ID NO: 43 | 103.7 | 159.9 | 97.7 | 150.7 |
| SEQ ID NO: 44 | 112.8 | 162.8 | 114.1 | 164.6 |

The results presented in Table 9 showed that most of the probes tested in the procedure gave strong hybridization signals and signal/noise ratios following interaction with each of the different target sequences. Notably, the result presented for the probe of SEQ ID NO:42 was obtained using the probe having its label positioned between nucleotides 12 and 13. However, excellent results were also achieved using the same probe sequence with alternatively positioned labels. More specifically, the signal/noise values for the collection of three probes of SEQ ID NO:42 ranged from about 218 up to about 296 for the HIV-1 target, and from about 220 to about 282 for the HIV-2 target. In addition to probes having the sequence of SEQ ID NO:42, the probes of SEQ ID NO:43 and SEQ ID NO:44 are also highly preferred for the detection of either or both of the HIV-1 and HIV-2 target nucleic acids. Of course, the complements of these sequences also are preferred alternatives.

Interestingly, the probes which performed well in the above-described assay all included target-complementary sequences of 21-26 contiguous bases contained within a consensus sequence given by AGGAAGTATACTGCATTTAC-CNTACC (SEQ ID NO:62), allowing for RNA and DNA equivalent bases, where "N" is any of A, C or I. The 26-mer probe of SEQ ID NO:41 did not perform well in the hybridization assay (see Table 9), and does not conform with the consensus. Notably, this poor-performing probe differed from the cross-reactive probe of SEQ ID NO:43, which performed well in the assay, by only a single base change. This illustrates the unusual and unexpected nature of the advantageously cross-reactive probes described above.

Highly preferred embodiments of the invention employ one or more of the cross-reactive probes of SEQ ID NO:42, SEQ ID NO:43 or SEQ ID NO:44 for detection of either HIV-1 or HIV-2 nucleic acids. However, kits in accordance with the invention can include in packaged combination: any probe having the sequence of SEQ ID NO:42, SEQ ID NO:43 or SEQ ID NO:44 and a set of oligonucleotide primers that are specific for HIV-1 (but not HIV-2) and/or a set of oligonucleotide primers that are specific for HIV-2 (but not HIV-1). An alternative kit can include in packaged combination: any probe having the sequence of SEQ ID NO:42, SEQ ID NO:43 or SEQ ID NO:44 and a set of oligonucleotide primers that are cross-reactive with HIV-1 and HIV-2, meaning primers that are capable of amplifying both HIV-1 and HIV-2 nucleic acids. The cross-reactive probe reagents are particularly preferred for use in methods wherein HIV-1 or HIV-2 amplicons synthesized using the cross-reactive amplification primers described in the following Example are detected.

Notably, in certain embodiments it will be desirable to employ probes having sequences appended to the 5' or 3' ends of the target-complementary probe sequences, which sequences are not complementary to, meaning that they do not hybridize to, the HIV-1 or HIV-2 amplicons. In these instances it is preferred for the overall length of the probe molecule to be up to 60, more preferrably up to 26, bases in length. Examples of appended sequences which are not complementary to the HIV-1 or HIV-2 amplicons include the "arm" sequences which comprise the "stem" portions of molecular beacons.

Preferred primer combinations for amplifying HIV-1 or HIV-2, or the combination of HIV-1 and HIV-2 nucleic acids were identified in a series of procedures that employed virions as the source of nucleic acid templates. Promoter-primers and opposite strand primers were screened in combination using the method described below. Although these procedures were particularly carried out using a Transcription Mediated Amplification (TMA) protocol, the primers disclosed herein may be used to produce amplicons by alternative in vitro nucleic acid amplification methods that will be familiar to those having an ordinary level of skill in the art. Tables 10 and 11 present the sequences of amplification primers that were used in the procedures described under Example 6. Notably, the primers of SEQ ID NOs:51-54 correspond to the primers of SEQ ID NOs:55-58, respectively, but further include upstream promoter sequences that are not complementary to the HIV-1 and HIV-2 targets.

TABLE 10

Sequences of Amplification Primers

| Sequence | Identifier |
|---|---|
| CTTAGATAAAGAITTCAGGAAGTATA | SEQ ID NO: 47 |
| CTTAGATAAAGATTTTAGGAAGTATA | SEQ ID NO: 48 |
| CTTAGATAAAGATTTTAGGCAGTATA | SEQ ID NO: 49 |
| CTTAGATAAAGATTTTAGGIAGTATA | SEQ ID NO: 50 |

TABLE 11

Sequences of Amplification Primers

| Feature | Sequence | Identifier |
|---|---|---|
| Target-complementary | TTGCTGGTGATCCCTTCCATCCTTGTGG | SEQ ID NO: 51 |
| Target-complementary | TTGCTGGTGATCCCTTCCATCCCTGTGG | SEQ ID NO: 52 |
| Target-complementary | TTGCTGGTGATCCTTTCCATCC | SEQ ID NO: 53 |
| Target-complementary | TTGCTGGTGATCCCTTCCATCC | SEQ ID NO: 54 |
| T7 Promoter-Primer | AATTTAATACGACTCACTATAGGGAGA TTGCTGGTGATCCCTTCCATCCTTGTGG | SEQ ID NO: 55 |
| T7 Promoter-Primer | AATTTAATACGACTCACTATAGGGAGA TTGCTGGTGATCCCTTCCATCCCTGTGG | SEQ ID NO: 56 |
| T7 Promoter-Primer | AATTTAATACGACTCACTATAGGGAGA TTGCTGGTGATCCTTTCCATCC | SEQ ID NO: 57 |
| T7 Promoter-Primer | AATTTAATACGACTCACTATAGGGAGA TTGCTGGTGATCCCTTCCATCC | SEQ ID NO: 58 |

Example 6 describes methods that identified primers useful for amplifying the p51 RT region of HIV-1 and/or HIV-2.

EXAMPLE 6

Identification of Amplification Primers

Tissue culture-derived HIV-2 B6 virus particles served as the source of HIV-2 template sequences in amplification reactions that employed paired sets of primers. Virus-negative serum was used to prepare diluted stocks containing either 100 copies/ml of the HIV-1 nucleic acid template, or 300 copies/ml of the HIV-2 nucleic acid template. Nucleic acids underwent specimen processing and target capture prior to amplification essentially according to the procedures disclosed in published International Patent Application No. PCT/US2000/18685, except that templates were captured using oligonucleotides described in the published international patent application identified by WO 03/106,714 for the capture of HIV-1 nucleic acids. Notably, capture oligonucleotides do not participate in the amplification or detection steps of the assay. Virus-containing samples having volumes of 0.5 ml were combined with a target-capture reagent to facilitate nucleic acid release and hybridization to capture oligonucleotides disposed on magnetic beads. TMA reactions were carried out essentially as described by Kacian et al., in U.S. Pat. No. 5,399,491, the disclosure of this U.S. patent having been incorporated by reference hereinabove. Promoter-primers included a T7 promoter sequence given by SEQ ID NO:39 upstream of a target-complementary sequence. Amplification reactions were conducted for various primer combinations using 15 pmoles of each primer in 100 µl of reaction buffer. Isolated target nucleic acids were combined with primers in a standard nucleic acid amplification buffer, heated to 60° C. for 10 minutes and then cooled to 42° C. to facilitate primer annealing. Moloney Murine Leukemia Virus (MMLV) reverse transcriptase (5,600 units/reaction) and T7 RNA polymerase (3,500 units/reaction) were then added to the mixtures. Amplification reactions were carried out in a Tris-buffered solution (pH 8.2 to 8.5) containing KCl, deoxyribonucleoside 5'-triphosphates, ribonucleoside 5'-triphosphates, N-Acetyl-L-Cysteine, and 5% (w/v) glycerol, as will be familiar to those having an ordinary level of skill in the art. After a one hour incubation at 42° C., the entire 100 µl amplification reaction was subjected to a hybridization assay essentially as described in Example 1 using a mixture of the above-described probe having the sequence of SEQ ID NO:42. For the purpose of this demonstration, a mixture of probes having the sequence of SEQ ID NO:42 with labels positioned between nucleotides 7 and 8, 11 and 12, and 12 and 13 were used in a ratio of 2:1:1, respectively. The probes were labeled with acridinium ester to specific activities of about $1\text{-}7\times10^8$ RLU/pmol and then used in amounts equivalent to about $2\times10^6$ RLU for each hybridization reaction. Specifically hybridized probe was quantified following chemical inactivation of the chemiluminescent label associated with non-hybridized probe in a homogeneous assay essentially as described in Example 1. Trials were conducted using replicates of 10. To be judged as a positive result, the chemiluminescent signal indicating probe hybridization must have exceeded 50,000 RLU in an assay.

Table 12 presents results from amplification procedures that were conducted using different combinations of amplification primers. Numerical values appearing in the table represent the percentage of positive trials.

TABLE 12

Amplification of HIV-1 and HIV-2 Polynucleotide Sequences Using Various Primer Combinations

| | | T7 Primer Target-Complementary Sequence | | | |
|---|---|---|---|---|---|
| non-T7 primer | Target (c/ml) | SEQ ID NO: 51 | SEQ ID NO: 52 | SEQ ID NO: 53 | SEQ ID NO: 54 |
| SEQ ID NO: 47 | HIV1 (100) | 100% | ND | 100% | ND |
| | HIV2 (300) | 100% | ND | 100% | ND |
| SEQ ID NO: 48 | HIV1 (100) | ND | 100% | ND | 100% |
| | HIV2 (300) | ND | 100% | ND | 100% |
| SEQ ID NO: 49 | HIV1 (100) | 100% | ND | 100% | ND |
| | HIV2 (300) | 100% | ND | 100% | ND |
| SEQ ID NO: 50 | HIV1 (100) | 100% | ND | 100% | ND |
| | HIV2 (300) | 100% | ND | 100% | ND |

"ND" indicates "not done" (primer pair not tested)

The results presented in Table 12 showed that all of the selected primer combinations were useful for detecting HIV-1 and HIV-2. The target-complementary portions of useful primers complementary to one strand of the target to be amplified included a sequence conforming to the consensus TTGCTGGTGATCCYTTCCATCC (SEQ ID NO:59), where position 14 is occupied by C or T, and had a length of up to 28 bases. In a preferred embodiment, the primer conformed to the consensus sequence TTGCTGGTGATCCYTTCCATCCYTGTGG (SEQ ID NO:60), where positions 14 and 23 are independently occupied by C or T. The preferred primers can further include optional 5' sequences which are non-complementary to the HIV-1 or HIV-2 target to be amplified. The target-complementary portions of useful opposite strand primers conformed to the consensus sequence CTTAGATAAAGANTTYAGGNAGTATA (SEQ ID NO:61), where position 13 is occupied by T or I, where position 16 is occupied by C or T, and where position 20 is occupied by A, C or I. Primers conforming to this consensus are also preferred for amplifying HIV-1 or HIV-2 target nucleic acids, and can further include optional 5' sequences which are non-complementary to the HIV-1 or HIV-2 target to be amplified. Notably, no false-positive reactions were observed in the procedures described above.

Although the foregoing Example illustrated an assay based on the combined use of cross-reactive primers and cross-reactive probes, the present invention also embraces embodiments wherein cross-reactive primers are used in combination, or packaged in a kit, with independent, analyte-specific HIV-1 and HIV-2 probes.

The following Example demonstrates that the cross-reactive p51 RT region primers disclosed herein were capable of amplifying HIV-1 and HIV-2 templates even when the procedures were performed in a reaction mixture that was capable of multiplex amplification of HIV-1, HIV-2, HBV and HCV. These results showed that the presence of primers specific for extraneous targets did not adversely impact detection of HIV-2.

Example 7 describes procedures that demonstrated how the invented primers could be combined in a multiplex nucleic acid amplification reaction capable of detecting HIV-1, HIV-2, HBV and HCV.

EXAMPLE 7

Amplification of HIV-2 Nucleic Acids in a Multiplex Assay

Primers having the sequences of SEQ ID NO:57 (target-complementary sequence of SEQ ID NO:53) and SEQ ID NO:49 were added to a reaction formulation that included primers capable of amplifying analytes that included either the combination of HBV and HCV, or the combination of HIV-1, HBV and HCV. Multiplex assay formulations for performing target capture, amplification and probe-based detection of these targets are disclosed in the published international patent application identified by WO 03/106714, the disclosure of which is incorporated by reference. As in Example 2, samples containing HIV-1 virions or HIV-2 virions were prepared by diluting high-titer stocks with virus-negative serum. Target capture and nucleic acid amplification reactions were performed using 0.5 ml of diluted virus sample, as described herein. Detection of HIV-2 amplicons was carried out using the probe reagent described in the preceding Example. Detection of HBV and HCV amplicons was carried out using labeled hybridization probes specific for those targets. Assays yielding specific hybridization signals of at least 50,000 RLUs were judged as being positive. Results from these procedures appear in Table 13.

TABLE 13

Detection of HIV-2 in a Multiplex Assay

| Target-Complementary Primer Sequences | Target | % Positive |
| --- | --- | --- |
| SEQ ID NO: 53 | HIV-1 Type B (100 c/ml) | 100% |
| SEQ ID NO: 49 | HIV-2 Type A (300 c/ml) | 100% |
| | HCV (60 c/ml) | 100% |
| | HBV (15 IU/ml) | 100% |

The results presented in Table 13 confirmed that the invented primers were capable of efficiently amplifying HIV-1 and HIV-2 target nucleic acids in multiplex reactions that were also capable of amplifying and detecting other viral targets. Also as shown in the table, low levels of the HBV (15 IU/ml) and HCV subtype 2b (60 copies/ml) targets were efficiently detected in the multiplex reactions capable of amplifying HIV-1 and HIV-2. Significantly, identical results were obtained using reaction conditions that included or omitted HIV-1 specific amplification primers. Thus, the disclosed HIV-1/-2 cross-reactive primers efficiently detected both HIV-1 and HIV-2, and did not interfere with amplification and detection of the remaining viral targets in the multiplex reaction.

This invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims.

What is claimed is:

1. A composition for amplifying both human immunodeficiency virus type 1 and 2 (HIV-1 and HIV-2) nucleic acids that may be present in a biological sample, comprising:
   (a) a first primer consisting of SEQ ID NO:59 and optionally, attached at the 5' end thereof, a first primer upstream sequence that comprises a restriction endonuclease cleavage site or an RNA polymerase promoter; and
   (b) a second primer consisting of SEQ ID NO:61 and optionally, attached at the 5' end thereof, a second primer upstream sequence that comprises a restriction endonuclease cleavage site or an RNA polymerase promoter.

2. The composition of claim 1, wherein said composition does not comprise a pair of HIV-2-specific primers for amplifying only said HIV-2 nucleic acid and not said HIV-1 nucleic acid.

3. The composition of claim 2, wherein said composition further comprises a pair of HIV-1-specific primers for amplifying only said HIV-1 nucleic acid and not said HIV-2 nucleic acid.

4. The composition of claim 1, wherein said composition further comprises a pair of HIV-1-specific primers for amplifying only said HIV-1 nucleic acid and not said HIV-2 nucleic acid.

5. The composition of claim 1, wherein said first primer and said second primer are each up to 60 bases in length.

6. The composition of claim 5, where said first primer consists of SEQ ID NO:53 and optionally, attached at the 5' end thereof, said first primer upstream sequence.

7. The composition of claim 5, where said first primer consists of SEQ ID NO:54 and optionally, attached at the 5' end thereof, said first primer upstream sequence.

8. The composition of claim 5, wherein the second primer is not attached to said second primer upstream sequence.

9. The composition of claim 8, wherein said second primer is selected from the group consisting of SEQ ID NO:47, SEQ ID NO:48, SEQ ID NO:49 and SEQ ID NO:50.

10. The composition of claim 5, wherein the first primer is not attached to said first primer upstream sequence.

11. The composition of claim 10, wherein the second primer is not attached to said second primer upstream sequence.

12. A method of determining whether a test sample contains at least one of HIV-1 nucleic acid and HIV-2 nucleic acid, said method comprising the steps of:
 (a) combining said test sample with a composition according to claim 1 to form a reaction mixture;
 (b) amplifying, in an in vitro nucleic acid amplification reaction, nucleic acid present in said reaction mixture of step (a); and
 (c) detecting an HIV-1 amplicon, and HIV-2 amplicon, or a combination of both amplicons synthesized in step (b), thereby determining that said test sample contains at least one of HIV-1 nucleic acid and HIV-2 nucleic acid.

13. The method of claim 12, wherein the detecting step comprises detecting in a hybridization reaction.

14. The method of claim 13, wherein said hybridization reaction in the detecting step comprises a cross-reactive probe which hybridizes independently to said HIV-1 amplicon and to said HIV-2 amplicon.

15. The method of claim 14, wherein said hybridization reaction in the detecting step further comprises an HIV-1 specific probe which hybridizes only to said HIV-1 amplicon and not to said HIV-2 amplicon.

16. The method of claim 12, wherein said in vitro nucleic acid amplification reaction in the amplifying step is a multiplex amplification reaction that can further amplify, with an assortment of target-specific primers, at least one nucleic acid which is different from HIV-1 and HIV-2.

17. The method of claim 16, wherein said at least one nucleic acid which is different from HIV-1 and HIV-2 is selected from the group consisting of HBV and HCV.

* * * * *

SEQUENCE LISTING

<160> NUMBER OF SEQ ID NOS: 62

<210> SEQ ID NO 1
<211> LENGTH: 19
<212> TYPE: DNA
<213> ORGANISM: Human immunodeficiency virus

<400> SEQUENCE: 1
acagcagtac aaatggcag                                              19

<210> SEQ ID NO 2
<211> LENGTH: 20
<212> TYPE: DNA

<213> ORGANISM: Human immunodeficiency virus

<400> SEQUENCE: 2
acaacagtac aaatggcagt                                                   20

<210> SEQ ID NO 3
<211> LENGTH: 20
<212> TYPE: DNA
<213> ORGANISM: Human immunodeficiency virus

<400> SEQUENCE: 3
acaatagtac taatggcagt                                                   20

<210> SEQ ID NO 4
<211> LENGTH: 22
<212> TYPE: DNA
<213> ORGANISM: Human immunodeficiency virus

<400> SEQUENCE: 4
ttaagacagc agtacaaatg gc                                                22

<210> SEQ ID NO 5
<211> LENGTH: 22
<212> TYPE: DNA
<213> ORGANISM: Human immunodeficiency virus

<400> SEQUENCE: 5
tagagacagc agtacaaatg gc                                                22

<210> SEQ ID NO 6
<211> LENGTH: 22
<212> TYPE: DNA
<213> ORGANISM: Human immunodeficiency virus
<220> FEATURE:
<221> NAME/KEY: misc_feature
<222> LOCATION: (16)..(16)
<223> OTHER INFORMATION: inosine

<400> SEQUENCE: 6
tagagacagc agtacnaatg gc                                                22

<210> SEQ ID NO 7
<211> LENGTH: 22
<212> TYPE: DNA
<213> ORGANISM: Human immunodeficiency virus
<220> FEATURE:
<221> NAME/KEY: misc_feature
<222> LOCATION: (16)..(16)
<223> OTHER INFORMATION: inosine

<400> SEQUENCE: 7
tagagacagt agtacnaatg gc                                                22

<210> SEQ ID NO 8
<211> LENGTH: 22
<212> TYPE: DNA
<213> ORGANISM: Human immunodeficiency virus

<400> SEQUENCE: 8
tagagacagc agtactaatg gc                                                22

<210> SEQ ID NO 9
<211> LENGTH: 22
<212> TYPE: DNA
<213> ORGANISM: Human immunodeficiency virus

```
<220> FEATURE:
<221> NAME/KEY: misc_feature
<222> LOCATION: (10)..(10)
<223> OTHER INFORMATION: inosine
<220> FEATURE:
<221> NAME/KEY: misc_feature
<222> LOCATION: (16)..(16)
<223> OTHER INFORMATION: inosine

<400> SEQUENCE: 9
tagagacagn agtacnaatg gc                                              22

<210> SEQ ID NO 10
<211> LENGTH: 17
<212> TYPE: DNA
<213> ORGANISM: Human immunodeficiency virus
<220> FEATURE:
<221> NAME/KEY: misc_feature
<222> LOCATION: (11)..(11)
<223> OTHER INFORMATION: position 11 occupied by A or T/U

<400> SEQUENCE: 10
acaryagtac waatggc                                                   17

<210> SEQ ID NO 11
<211> LENGTH: 27
<212> TYPE: DNA
<213> ORGANISM: Human immunodeficiency virus

<400> SEQUENCE: 11
atttcttgtt ctgtggtaat catgttg                                         27

<210> SEQ ID NO 12
<211> LENGTH: 32
<212> TYPE: DNA
<213> ORGANISM: Human immunodeficiency virus

<400> SEQUENCE: 12
ttgtttttgt aatagttgta tttcttgttc tg                                   32

<210> SEQ ID NO 13
<211> LENGTH: 44
<212> TYPE: DNA
<213> ORGANISM: Human immunodeficiency virus

<400> SEQUENCE: 13
gtttgtatgt ctgttgctat tatgtctatt agtctttctg ctgg                      44

<210> SEQ ID NO 14
<211> LENGTH: 38
<212> TYPE: DNA
<213> ORGANISM: Human immunodeficiency virus

<400> SEQUENCE: 14
gtttgtatgt ctgttgctat catgttgatt attctttc                             38

<210> SEQ ID NO 15
<211> LENGTH: 35
<212> TYPE: DNA
<213> ORGANISM: Human immunodeficiency virus

<400> SEQUENCE: 15
atttgttttt gtaattcttg tatttctatg tctgt                                35

<210> SEQ ID NO 16
```

```
<211> LENGTH: 28
<212> TYPE: DNA
<213> ORGANISM: Human immunodeficiency virus

<400> SEQUENCE: 16
gtttgtatgt ctgttgctat tatgtcta                                           28

<210> SEQ ID NO 17
<211> LENGTH: 54
<212> TYPE: DNA
<213> ORGANISM: Artificial
<220> FEATURE:
<223> OTHER INFORMATION: T7 promoter-primer

<400> SEQUENCE: 17
aatttaatac gactcactat agggagaatt tcttgttctg tggtaatcat gttg             54

<210> SEQ ID NO 18
<211> LENGTH: 59
<212> TYPE: DNA
<213> ORGANISM: Artificial
<220> FEATURE:
<223> OTHER INFORMATION: T7 promoter-primer

<400> SEQUENCE: 18
aatttaatac gactcactat agggagattg tttttgtaat agttgtattt cttgttctg        59

<210> SEQ ID NO 19
<211> LENGTH: 71
<212> TYPE: DNA
<213> ORGANISM: Artificial
<220> FEATURE:
<223> OTHER INFORMATION: T7 promoter-primer

<400> SEQUENCE: 19
aatttaatac gactcactat agggagagtt tgtatgtctg ttgctattat gtctattagt       60
ctttctgctg g                                                            71

<210> SEQ ID NO 20
<211> LENGTH: 65
<212> TYPE: DNA
<213> ORGANISM: Artificial
<220> FEATURE:
<223> OTHER INFORMATION: T7 promoter-primer

<400> SEQUENCE: 20
aatttaatac gactcactat agggagagtt tgtatgtctg ttgctatcat gttgattatt       60
ctttc                                                                   65

<210> SEQ ID NO 21
<211> LENGTH: 62
<212> TYPE: DNA
<213> ORGANISM: Artificial
<220> FEATURE:
<223> OTHER INFORMATION: T7 promoter-primer

<400> SEQUENCE: 21
aatttaatac gactcactat agggagaatt tgttttgta attcttgtat ttctatgtct        60
gt                                                                      62

<210> SEQ ID NO 22
<211> LENGTH: 55
<212> TYPE: DNA
<213> ORGANISM: Artificial
```

```
<220> FEATURE:
<223> OTHER INFORMATION: T7 promoter-primer

<400> SEQUENCE: 22
aatttaatac gactcactat agggagagtt tgtatgtctg ttgctattat gtcta         55

<210> SEQ ID NO 23
<211> LENGTH: 22
<212> TYPE: DNA
<213> ORGANISM: Human immunodeficiency virus

<400> SEQUENCE: 23
cctgaatttt aaagaagggg gg                                              22

<210> SEQ ID NO 24
<211> LENGTH: 24
<212> TYPE: DNA
<213> ORGANISM: Human immunodeficiency virus
<220> FEATURE:
<221> NAME/KEY: misc_feature
<222> LOCATION: (22)..(22)
<223> OTHER INFORMATION: inosine

<400> SEQUENCE: 24
ccagaatttt aaagaagggg gngg                                            24

<210> SEQ ID NO 25
<211> LENGTH: 24
<212> TYPE: DNA
<213> ORGANISM: Human immunodeficiency virus
<220> FEATURE:
<221> NAME/KEY: misc_feature
<222> LOCATION: (22)..(22)
<223> OTHER INFORMATION: inosine

<400> SEQUENCE: 25
ccacaatttt aaagaagggg gngg                                            24

<210> SEQ ID NO 26
<211> LENGTH: 24
<212> TYPE: DNA
<213> ORGANISM: Human immunodeficiency virus
<220> FEATURE:
<221> NAME/KEY: misc_feature
<222> LOCATION: (22)..(22)
<223> OTHER INFORMATION: inosine

<400> SEQUENCE: 26
cctgaatttt aaagaagggg gngg                                            24

<210> SEQ ID NO 27
<211> LENGTH: 22
<212> TYPE: DNA
<213> ORGANISM: Human immunodeficiency virus

<400> SEQUENCE: 27
catgaatttt aaagaagggg ga                                              22

<210> SEQ ID NO 28
<211> LENGTH: 22
<212> TYPE: DNA
<213> ORGANISM: Human immunodeficiency virus
<220> FEATURE:
<221> NAME/KEY: misc_feature
<222> LOCATION: (18)..(18)
<223> OTHER INFORMATION: inosine
```

<400> SEQUENCE: 28 cctgaattt aaaagaaggg gg                                                    22

<210> SEQ ID NO 29
<211> LENGTH: 22
<212> TYPE: DNA
<213> ORGANISM: Human immunodeficiency virus
<220> FEATURE:
<221> NAME/KEY: misc_feature
<222> LOCATION: (3)..(3)
<223> OTHER INFORMATION: inosine

<400> SEQUENCE: 29 ccngaattt aaaagaaggg gg                                                    22

<210> SEQ ID NO 30
<211> LENGTH: 22
<212> TYPE: DNA
<213> ORGANISM: Human immunodeficiency virus
<220> FEATURE:
<221> NAME/KEY: misc_feature
<222> LOCATION: (3)..(3)
<223> OTHER INFORMATION: inosine
<220> FEATURE:
<221> NAME/KEY: misc_feature
<222> LOCATION: (4)..(4)
<223> OTHER INFORMATION: inosine

<400> SEQUENCE: 30 ccnnaattt aaaagaaggg gg                                                    22

<210> SEQ ID NO 31
<211> LENGTH: 23
<212> TYPE: DNA
<213> ORGANISM: Human immunodeficiency virus
<220> FEATURE:
<221> NAME/KEY: misc_feature
<222> LOCATION: (7)..(7)
<223> OTHER INFORMATION: inosine
<220> FEATURE:
<221> NAME/KEY: misc_feature
<222> LOCATION: (10)..(10)
<223> OTHER INFORMATION: inosine
<220> FEATURE:
<221> NAME/KEY: misc_feature
<222> LOCATION: (17)..(17)
<223> OTHER INFORMATION: inosine
<220> FEATURE:
<221> NAME/KEY: misc_feature
<222> LOCATION: (21)..(21)
<223> OTHER INFORMATION: inosine

<400> SEQUENCE: 31
aaagaanggn ggggatnggg ngg                                                  23

<210> SEQ ID NO 32
<211> LENGTH: 23
<212> TYPE: DNA
<213> ORGANISM: Human immunodeficiency virus
<220> FEATURE:
<221> NAME/KEY: misc_feature
<222> LOCATION: (7)..(7)
<223> OTHER INFORMATION: inosine
<220> FEATURE:
<221> NAME/KEY: misc_feature
<222> LOCATION: (10)..(10)
<223> OTHER INFORMATION: inosine
<220> FEATURE:
<221> NAME/KEY: misc_feature
<222> LOCATION: (21)..(21)
<223> OTHER INFORMATION: inosine

```
<400> SEQUENCE: 32
aaagaanggn ggggattggg ngg                                           23

<210> SEQ ID NO 33
<211> LENGTH: 29
<212> TYPE: DNA
<213> ORGANISM: Human immunodeficiency virus
<220> FEATURE:
<221> NAME/KEY: misc_feature
<222> LOCATION: (18)..(18)
<223> OTHER INFORMATION: inosine

<400> SEQUENCE: 33
aattttaaaa gaagaggngg gattggggg                                     29

<210> SEQ ID NO 34
<211> LENGTH: 22
<212> TYPE: DNA
<213> ORGANISM: Human immunodeficiency virus
<220> FEATURE:
<221> NAME/KEY: misc_feature
<222> LOCATION: (19)..(19)
<223> OTHER INFORMATION: inosine

<400> SEQUENCE: 34
caattttaaa agaaggggng gg                                            22

<210> SEQ ID NO 35
<211> LENGTH: 22
<212> TYPE: DNA
<213> ORGANISM: Human immunodeficiency virus
<220> FEATURE:
<221> NAME/KEY: misc_feature
<222> LOCATION: (16)..(16)
<223> OTHER INFORMATION: inosine
<220> FEATURE:
<221> NAME/KEY: misc_feature
<222> LOCATION: (21)..(21)
<223> OTHER INFORMATION: inosine

<400> SEQUENCE: 35
gaattttaaa agaagngggg ng                                            22

<210> SEQ ID NO 36
<211> LENGTH: 22
<212> TYPE: RNA
<213> ORGANISM: Human immunodeficiency virus
<220> FEATURE:
<221> NAME/KEY: misc_feature
<222> LOCATION: (19)..(19)
<223> OTHER INFORMATION: inosine

<400> SEQUENCE: 36
gaauuuaaaa agaaggggng gg                                            22

<210> SEQ ID NO 37
<211> LENGTH: 30
<212> TYPE: DNA
<213> ORGANISM: Human immunodeficiency virus

<400> SEQUENCE: 37
tccccccttt tcttttaaaa ttgtggatga                                    30

<210> SEQ ID NO 38
<211> LENGTH: 30
<212> TYPE: DNA
```

<213> ORGANISM: Human immunodeficiency virus

<400> SEQUENCE: 38
ttcctcccct tcttttaaaa ttcatgcaat                     30

<210> SEQ ID NO 39
<211> LENGTH: 27
<212> TYPE: DNA
<213> ORGANISM: Artificial
<220> FEATURE:
<223> OTHER INFORMATION: T7 phage promoter sequence

<400> SEQUENCE: 39
aatttaatac gactcactat agggaga                       27

<210> SEQ ID NO 40
<211> LENGTH: 22
<212> TYPE: DNA
<213> ORGANISM: Artificial
<220> FEATURE:
<223> OTHER INFORMATION: Artificial HIV consensus sequence
<220> FEATURE:
<221> NAME/KEY: misc_feature
<222> LOCATION: (10)..(10)
<223> OTHER INFORMATION: position occupied by C, T or I (inosine)
<220> FEATURE:
<221> NAME/KEY: misc_feature
<222> LOCATION: (16)..(16)
<223> OTHER INFORMATION: position occupied by T or I (inosine)

<400> SEQUENCE: 40
tagagacagn agtacnaatg gc                            22

<210> SEQ ID NO 41
<211> LENGTH: 26
<212> TYPE: RNA
<213> ORGANISM: Human immunodeficiency virus
<220> FEATURE:
<221> NAME/KEY: misc_feature
<222> LOCATION: (22)..(22)
<223> OTHER INFORMATION: inosine

<400> SEQUENCE: 41
aggcaguaua cugcauuuac cnuacc                        26

<210> SEQ ID NO 42
<211> LENGTH: 21
<212> TYPE: DNA
<213> ORGANISM: Human immunodeficiency virus

<400> SEQUENCE: 42
gtatactgca tttaccctac c                             21

<210> SEQ ID NO 43
<211> LENGTH: 26
<212> TYPE: RNA
<213> ORGANISM: Human immunodeficiency virus
<220> FEATURE:
<221> NAME/KEY: misc_feature
<222> LOCATION: (22)..(22)
<223> OTHER INFORMATION: inosine

<400> SEQUENCE: 43
aggaaguaua cugcauuuac cnuacc                        26

<210> SEQ ID NO 44
<211> LENGTH: 26

```
<212> TYPE: RNA
<213> ORGANISM: Human immunodeficiency virus

<400> SEQUENCE: 44
aggaaguaua cugcauuuac cauacc                                          26

<210> SEQ ID NO 45
<211> LENGTH: 27
<212> TYPE: RNA
<213> ORGANISM: Human immunodeficiency virus

<400> SEQUENCE: 45
cuagguaugg uaaaugcagu auacuuc                                         27

<210> SEQ ID NO 46
<211> LENGTH: 25
<212> TYPE: RNA
<213> ORGANISM: Human immunodeficiency virus

<400> SEQUENCE: 46
gaugguaggg uaaaugcagu auacu                                           25

<210> SEQ ID NO 47
<211> LENGTH: 26
<212> TYPE: DNA
<213> ORGANISM: Human immunodeficiency virus
<220> FEATURE:
<221> NAME/KEY: misc_feature
<222> LOCATION: (13)..(13)
<223> OTHER INFORMATION: inosine

<400> SEQUENCE: 47
cttagataaa ganttcagga agtata                                          26

<210> SEQ ID NO 48
<211> LENGTH: 26
<212> TYPE: DNA
<213> ORGANISM: Human immunodeficiency virus

<400> SEQUENCE: 48
cttagataaa gattttagga agtata                                          26

<210> SEQ ID NO 49
<211> LENGTH: 26
<212> TYPE: DNA
<213> ORGANISM: Human immunodeficiency virus

<400> SEQUENCE: 49
cttagataaa gattttaggc agtata                                          26

<210> SEQ ID NO 50
<211> LENGTH: 26
<212> TYPE: DNA
<213> ORGANISM: Human immunodeficiency virus
<220> FEATURE:
<221> NAME/KEY: misc_feature
<222> LOCATION: (20)..(20)
<223> OTHER INFORMATION: inosine

<400> SEQUENCE: 50
cttagataaa gattttaggn agtata                                          26

<210> SEQ ID NO 51
<211> LENGTH: 28
<212> TYPE: DNA
```

<213> ORGANISM: Human immunodeficiency virus

<400> SEQUENCE: 51
ttgctggtga tcccttccat ccttgtgg         28

<210> SEQ ID NO 52
<211> LENGTH: 28
<212> TYPE: DNA
<213> ORGANISM: Human immunodeficiency virus

<400> SEQUENCE: 52
ttgctggtga tcccttccat ccctgtgg         28

<210> SEQ ID NO 53
<211> LENGTH: 22
<212> TYPE: DNA
<213> ORGANISM: Human immunodeficiency virus

<400> SEQUENCE: 53
ttgctggtga tcctttccat cc         22

<210> SEQ ID NO 54
<211> LENGTH: 22
<212> TYPE: DNA
<213> ORGANISM: Human immunodeficiency virus

<400> SEQUENCE: 54
ttgctggtga tcccttccat cc         22

<210> SEQ ID NO 55
<211> LENGTH: 55
<212> TYPE: DNA
<213> ORGANISM: Artificial
<220> FEATURE:
<223> OTHER INFORMATION: T7 promoter-primer

<400> SEQUENCE: 55
aatttaatac gactcactat agggagattg ctggtgatcc cttccatcct tgtgg         55

<210> SEQ ID NO 56
<211> LENGTH: 55
<212> TYPE: DNA
<213> ORGANISM: Artificial
<220> FEATURE:
<223> OTHER INFORMATION: T7 promoter-primer

<400> SEQUENCE: 56
aatttaatac gactcactat agggagattg ctggtgatcc cttccatccc tgtgg         55

<210> SEQ ID NO 57
<211> LENGTH: 49
<212> TYPE: DNA
<213> ORGANISM: Artificial
<220> FEATURE:
<223> OTHER INFORMATION: T7 promoter-primer

<400> SEQUENCE: 57
aatttaatac gactcactat agggagattg ctggtgatcc tttccatcc         49

<210> SEQ ID NO 58
<211> LENGTH: 49
<212> TYPE: DNA
<213> ORGANISM: Artificial
<220> FEATURE:
<223> OTHER INFORMATION: T7 promoter-primer -continued

```
<400> SEQUENCE: 58
aatttaatac gactcactat agggagattg ctggtgatcc cttccatcc            49

<210> SEQ ID NO 59
<211> LENGTH: 22
<212> TYPE: DNA
<213> ORGANISM: Human immunodeficiency virus

<400> SEQUENCE: 59
ttgctggtga tccyttccat cc                                         22

<210> SEQ ID NO 60
<211> LENGTH: 28
<212> TYPE: DNA
<213> ORGANISM: Human immunodeficiency virus

<400> SEQUENCE: 60
ttgctggtga tccyttccat ccytgtgg                                   28

<210> SEQ ID NO 61
<211> LENGTH: 26
<212> TYPE: DNA
<213> ORGANISM: Human immunodeficiency virus
<220> FEATURE:
<221> NAME/KEY: misc_feature
<222> LOCATION: (13)..(13)
<223> OTHER INFORMATION: position occupied by T or I (inosine)
<220> FEATURE:
<221> NAME/KEY: misc_feature
<222> LOCATION: (20)..(20)
<223> OTHER INFORMATION: position occupied by A, C or I (inosine)

<400> SEQUENCE: 61
cttagataaa ganttyaggn agtata                                     26

<210> SEQ ID NO 62
<211> LENGTH: 26
<212> TYPE: DNA
<213> ORGANISM: Human immunodeficiency virus
<220> FEATURE:
<221> NAME/KEY: misc_feature
<222> LOCATION: (22)..(22)
<223> OTHER INFORMATION: position occupied by A, C or I (inosine)

<400> SEQUENCE: 62
aggaagtata ctgcatttac cntacc                                     26
```